(12) United States Patent
Sen Gupta et al.

(10) Patent No.: US 8,838,393 B2
(45) Date of Patent: Sep. 16, 2014

(54) SYSTEMS AND METHODS FOR TOPOGRAPHIC ANALYSIS

(75) Inventors: Ananya Sen Gupta, Somerville, MA (US); Christopher M. Reddy, Falmouth, MA (US); Robert Nelson, Woods Hole, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 0 days.

(21) Appl. No.: 13/437,759

(22) Filed: Apr. 2, 2012

(65) Prior Publication Data

US 2013/0060477 A1    Mar. 7, 2013

Related U.S. Application Data

(60) Provisional application No. 61/470,790, filed on Apr. 1, 2011, provisional application No. 61/514,268, filed on Aug. 2, 2011.

(51) Int. Cl.
*G01N 33/48* (2006.01)
*G01N 30/86* (2006.01)
*G06F 19/00* (2011.01)
*G01N 30/46* (2006.01)

(52) U.S. Cl.
CPC .......... *G01N 30/8686* (2013.01); *G06F 19/707* (2013.01); *G06F 19/703* (2013.01); *G01N 30/463* (2013.01)
USPC ....................................................... 702/19

(58) Field of Classification Search
None
See application file for complete search history.

(56) References Cited

U.S. PATENT DOCUMENTS

2005/0065732 A1    3/2005    Tilton et al.
2007/0020662 A1    1/2007    Cima et al.

OTHER PUBLICATIONS

Chae et al., "An iterative block-shifting approach to retention time alignment that preserves the shape and area of gas chromatography-mass spectrometry peaks," BMC Bioinformatics 2008, 9(Suppl 9) S15.
Ventura et al., "Analysis of petroleum compositional similarity using multiway principal components analysis (MPCA) with comprehensive two-dimensional gas chromatographic data," Journal of Chromatography A 1218:2584-2592 (2011).
Ventura et al., "Compound class oil fingerprinting techniques using comprehensive two-dimensional gas chromatography (GCxGC)," Organic Geochemistry 41:1026-1035 (2010).
International Search Report for PCT/US2012/031898 dated Apr. 2, 2012.

*Primary Examiner* — Eric S Dejong
(74) *Attorney, Agent, or Firm* — Ropes & Gray LLP

(57) ABSTRACT

The systems and methods described herein provide a scientific and analytical basis for the following: (a) collective interpretation of the entire spectrum of chromatographic data, e.g., GCxGC two-dimensional data, with capability of operating at multi-resolution over bigger or smaller sub-regions of the two-dimensional data, (b) given two or more samples that are from the same source, and some samples from clearly different sources, quantitatively estimate where the fingerprint of the source lies, (c) given a source signature template, an unknown sample can be compared to decide whether it is related to, and if so, to what degree, to this source, and (d) given two source signature templates, the templates can be compared to determine how related is one source to the other.

30 Claims, 21 Drawing Sheets
(7 of 21 Drawing Sheet(s) Filed in Color)

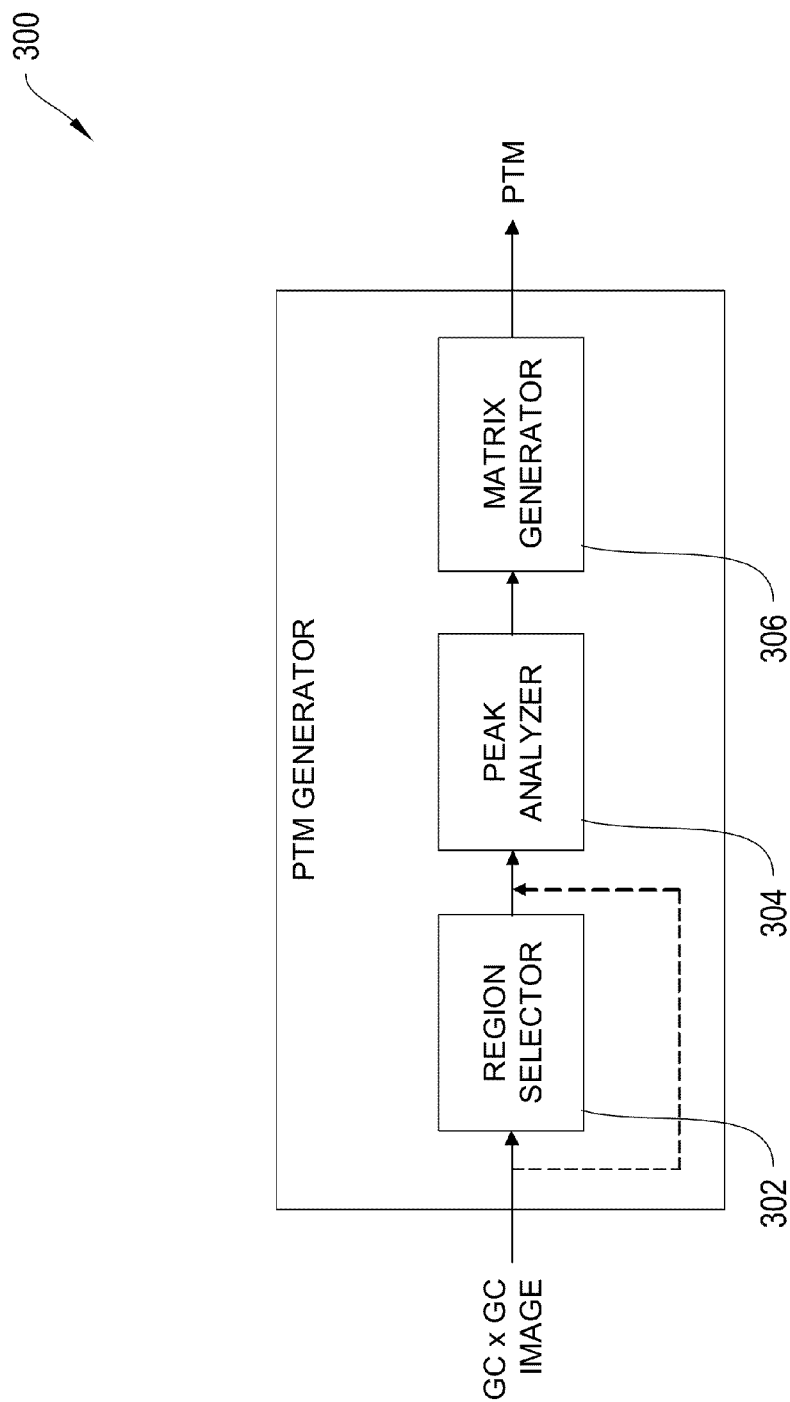

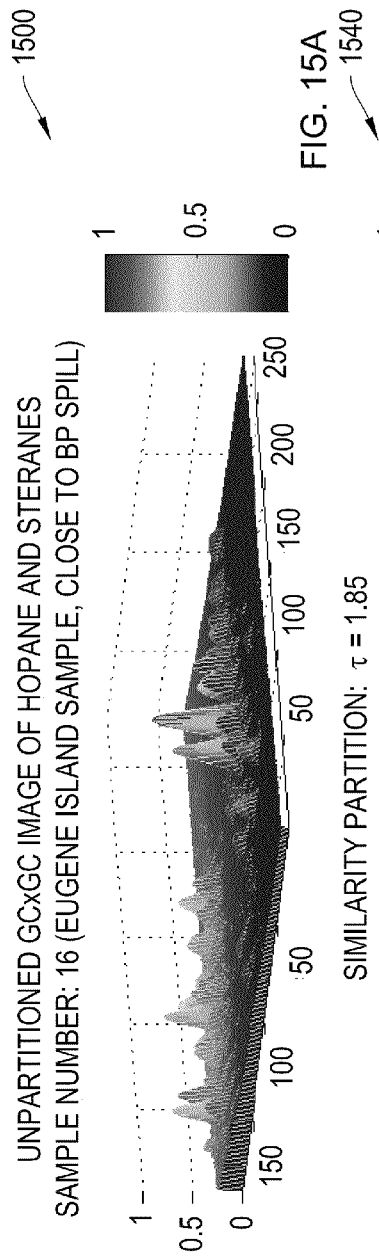

SYSTEMS AND METHODS FOR TOPOGRAPHIC ANALYSIS

CROSS-REFERENCE TO RELATED APPLICATIONS

This application claims priority to and the benefit of U.S. Provisional Patent Application Ser. No. 61/470,790, filed Apr. 1, 2011 and entitled "Methods for Topography Filtering," and U.S. Provisional Patent Application Ser. No. 61/514,268, filed Aug. 2, 2011 and entitled "System and Method for Interpreting Information," the entire contents of each of which are incorporated herein by reference.

BACKGROUND

The need for powerful analytics tools is not limited to any one industry or field, but there is an especially strong need for such tools to aid in analyzing chemical mixtures, including quantitatively identifying the relative distributions between the constituent chemical compounds that comprise such mixtures. Chromatography, and other such methods, provide rich detail, but such detail is only as useful as the capability of tools used to analyze it. Existing tools range from "eye-balling" chromatograms to merely observing the relative ratios of a few compounds among potentially hundreds of chemicals and compounds within a mixture. Further, the existing analytical chemistry techniques that analyze the relative abundance of a few well known major compounds fail to quantify the inter-relationship between the major as well as minor (e.g., rarely investigated) constituent compounds in a complex mixture.

For example, in petroleum mixtures or oil samples, hundreds of hydrocarbons are detected in a two-dimensional gas chromatography (GC×GC) dataset, but current approaches to "fingerprint" oil samples rely solely on comparing the relative abundances of molecular fossils (biomarkers) occurring within the oil sample. This approach is now decades old and may not be capable of working in the Gulf where researchers are currently faced with the BP spill problem of how to disentangle the BP oil in environmental samples from closely related natural oil seeps and other sources. This problem is not limited to the BP spill but extends to many other spills of distilled products and crudes. Further, additional problems remains. For example, the systems existing as they are today lack the ability to detect connectivity between wells based on oil sample fingerprinting.

Thus, in addition to the need for powerful high-resolution separation of compounds, there is a specific and clear need for analytical techniques and informational methods that can provide comprehensive interpretation for the rich intricate high-volume GC×GC data. Additionally, there is a specific and clear need to account quantitatively for the distinctions and similarities exhibited across all of the constituent compounds in a chemical mixture.

SUMMARY

Fingerprint analysis of an oil sample to identify potential sources is critical to the petroleum industry as well as to environmental chemistry. Knowing how closely related petroleum sources are plays a key role in the placement of oil wells, which cost over a billion dollars to construct and develop in deep water regimes. From an environmental perspective, advanced signal processing may enable chemists to fingerprint and identify one source of oil from other petroleum sources and quantitatively map the degree of environmental impact from an oil spill disaster. For example, this is a major challenge in regions at intermediate distance from the Deepwater Horizon disaster site, where other sources of oil may be present due to natural oil seeps or other petroleum industry activities. Thus successful fingerprinting may save the oil industry billions of dollars and environmental impact by avoiding unnecessary and risky drilling. Despite continued interest in petroleum fingerprinting, analytical research in the last three decades has been limited to interpreting the relative ratios of a few important compounds among hundreds of hydrocarbons that collectively constitute petroleum. This traditional approach enables distinction between sources that exhibit significant differences in the distribution of the major compounds, but fails to ensure separation between geologically related sources that share significant correlation between their fingerprints, i.e., most of the major compounds occur in similar proportions. Even in the case where traditional analysis provides some quantitative separation between sources, it does not provide insight into what portion of the molecular mixture constitutes the petroleum fingerprint for a particular source.

The systems and methods described herein involve novel signal processing techniques that give viable and scalable solutions to the above-described problems. The techniques may employ comprehensive two-dimensional gas chromatography (GC×GC) images to provide unprecedented information on compounds in oil and processes that act on them. For example, the systems and methods described herein include petroleum fingerprinting based on peak topography mapping of comprehensive two-dimensional chromatography (GC×GC) images. The proposed fingerprint of an oil sample or a petroleum source lies in the collective interpretation of the intricate network of peaks in the GC×GC image, rather than analysis of only a few well-known peaks, corresponding to major compounds. The collective interpretation of the network of peaks, distributed across the GC×GC topography, is performed using peak topography maps (PTMs), a novel feature representation based on the peak distribution of well-known major compounds as well as less-explored minor compounds. Several comparison metrics may then be used for peak-to-peak comparisons between PTMs of different oil samples. One advantage of such collective interpretation lies in quantifying the match between two samples or injections as a threshold-driven analog measure rather than a binary decision based on few major compounds. Since both major and minor compounds are used for comparison of samples, the more complex samples having several compounds offer additional information for comparison than samples having fewer compounds. Therefore, another advantage of such collective interpretation includes increased robustness with increasing complexity of samples under consideration. Furthermore, to enable successful comparison between GC×GC image peaks stored as nodes in the PTMs, the systems and methods described herein include alignment techniques to match two PTMs against each other, thereby ensuring that the same compound gets compared between two PTM nodes independent of any chromatographic variability shifting the peak locations in the GC×GC images under consideration.

The systems and methods described herein further provide quantitative measures and visual representations, such as topography partitioning, for direct comparison based on peak-to-peak comparison metrics between PTMs of different chemical mixtures, e.g., different oil samples. This is a topography-based measure that combines the interpretation offered by traditional comparison of a few well-known peaks with several additional less-explored peaks that are typically unused for interpretation of chromatography images. The topography partitioning measure visually represents peak-to-peak comparisons between a source PTM and a target PTM by splitting the target PTM into two graphs: a similarity partition graph that illustrates peaks similar to the source PTM, and a dissimilarity partition graph that illustrates peaks dissimilar to the source PTM. The split may be accomplished by computing the percentage of the total spread of peaks within the target PTM dataset that falls within or outside the similarity threshold of the source PTM. The topography partitioning measure may aid in cases where a compound is present in one PTM and absent or ill-formed in the other, and help distinguish between samples that have similarity between the common peaks but have significant components in the dissimilarity partition. Further details on topography partitioning are provided herein with reference to one or more illustrative embodiments.

More particularly, in one aspect, the systems and methods described herein include methods for comparing samples, each having a plurality of compounds. The methods may include receiving, at a peak topography map (PTM) generator, a reference dataset representing a relative separation of a plurality of compounds included in a reference sample. The reference dataset may have topographic variations and may include a plurality of peaks representing one or more compounds. The methods may include receiving, at the PTM generator, a target dataset representing a relative separation of a plurality of compounds included in a target sample. The target dataset may have topographic variations and may include a plurality of peaks representing one or more compounds. The methods may further include identifying, at a peak analyzer, peak information for each peak in the reference dataset and the target dataset. Peak information for each peak may include at least one of a peak height, a peak location, a peak volume, and a peak order. The methods may include determining, at a PTM analyzer, a similarity index based on the identified peak information. In certain embodiments, the methods include generating, at a topography partitioner, a similarity partition based on the similarity index that represents a similarity in topographic variations between the reference dataset and the target dataset and a dissimilarity partition based on the similarity index that represents a dissimilarity in topographic variations between the reference dataset and the target dataset. In certain embodiments, the similarity partition includes one or more peaks from the target dataset that are similar to corresponding peaks in the reference data set.

The methods may further include receiving, at a region selector, an indication of a region of interest in the reference dataset and extracting, at the region selector, the region of interest for use as the reference dataset. The reference dataset and the target dataset may include one of a comprehensive two-dimensional gas chromatogram, a one-dimensional gas chromatogram, a gas chromatogram and mass-spectrogram (GC-MS), a liquid chromatogram and gas chromatogram (LC×GC), and a two-dimensional liquid chromatogram (LC×LC). The reference sample and the target sample may be oil samples, and each sample may include a plurality of biomarker compounds. In certain embodiments, the plurality of biomarker compounds includes hopanes and steranes. The reference dataset and the target dataset may include substantially all peaks representing their respective plurality of compounds. The method may further comprise receiving a comparison threshold at the PTM analyzer, and determining the similarity index based on the comparison threshold.

In another aspect, the systems and methods described herein include systems for comparing samples, each having a plurality of compounds. The systems include a peak topography map (PTM) generator, a peak analyzer, a PTM analyzer, and a topography partitioner. The peak topography map (PTM) generator may be configured to receive a reference dataset representing a relative separation of a plurality of compounds included in a reference sample. The reference dataset may have topographic variations includes a plurality of peaks representing one or more compounds. The PTM generator may be configured to receive a target dataset representing a relative separation of a plurality of compounds included in a target sample. The target dataset may have topographic variations includes a plurality of peaks representing one or more compounds. The peak analyzer may be configured to identify peak information for each peak in the reference dataset and the target dataset. The peak information for each peak may include at least one of a peak height, a peak location, a peak volume, and a peak order. The PTM analyzer may be configured to determine a similarity index based on the identified peak information. The topography partitioner may be configured to generate a similarity partition based on the similarity index that represents a similarity in topographic variations between the reference dataset and the target dataset and/or a dissimilarity partition based on the similarity index that represents a dissimilarity in topographic variations between the reference dataset and the target dataset. In certain embodiments, the similarity partition includes one or more peaks from the target dataset that are similar to corresponding peaks in the reference data set. The system may further include a region selector configured to receive an indication of a region of interest in the reference dataset and extract the region of interest for use as the reference dataset. In certain embodiments, the PTM analyzer is further configured to receive a comparison threshold, and determine the similarity index based on the comparison threshold.

In another aspect, the systems and methods described herein include methods for comparing samples, each having a plurality of compounds. The methods may include receiving, at a PTM generator, a reference dataset representing a relative separation of a plurality of compounds included in a reference sample, wherein the reference dataset has topographic variations includes a plurality of peaks representing one or more compounds, and a target dataset representing a relative separation of a plurality of compounds included in a target sample, wherein the target dataset has topographic variations includes a plurality of peaks representing one or more compounds. The methods may further include identifying, at a peak analyzer, peak information for each peak in the reference dataset and the target dataset, wherein peak information for each peak includes at least one of a peak height, a peak location, a peak volume, and a peak order. The methods may include generating, at a matrix generator, a reference PTM based on the identified reference peak information, the reference PTM having one or more nodes storing reference peak information, and a target PTM based on the identified target peak information, the target PTM having one or more nodes storing target peak information. The methods may include determining, at a PTM analyzer, a similarity index based on peak information stored in the reference PTM and the target PTM.

In certain embodiments, the methods include aligning, at a node aligner, the reference PTM and the target PTM based on comparison metrics of selected corresponding nodes from each PTM. In such embodiments, aligning the reference PTM and the target PTM may comprise inserting one or more nodes in proximity of the selected nodes in one of the reference PTM and the target PTM based on the comparison metrics of the selected nodes.

In certain embodiments, the methods may include selecting, at a cluster analyzer, a subsection of one of the reference PTM and target PTM, and analyzing, at the cluster analyzer, peak information of a plurality of nodes in the subsection. In response to determining one or more nodes having lower peaks in proximity to at least one node having a higher peak, the methods may include generating, at the cluster analyzer, a clustered node combining the nodes having the lower peaks and the at least one node having the higher peak.

In certain embodiments, the methods include generating, at a topography partitioner, a similarity partition based on the similarity index that represents a similarity in topographic variations between the reference dataset and the target dataset and a dissimilarity partition based on the similarity index that represents a dissimilarity in topographic variations between the reference dataset and the target dataset.

In yet another aspect, the systems and methods described herein include a system for comparing samples. The systems may include a peak topography map (PTM) generator, a peak analyzer, a matrix generator, and a PTM analyzer. The PTM generator may be configured to receive a reference dataset representing a relative separation of a plurality of compounds included in a reference sample, wherein the reference dataset has topographic variations includes a plurality of peaks representing one or more compounds, and a target dataset representing a relative separation of a plurality of compounds included in a target sample, wherein the target dataset has topographic variations includes a plurality of peaks representing one or more compounds. The peak analyzer may be configured to identify peak information for each peak in the reference dataset and the target dataset, wherein peak information for each peak includes at least one of a peak height, a peak location, a peak volume, and a peak order. The matrix generator may be configured to generate a reference peak topography map (PTM) based on the identified reference peak information, the reference PTM having one or more nodes storing reference peak information, and a target PTM based on the identified target peak information, the target PTM having one or more nodes storing target peak information. The PTM analyzer may be configured to determine a similarity index based on peak information stored in the reference PTM and the target PTM.

In certain embodiments, the systems and methods include a node aligner configured to align the reference PTM and the target PTM based on comparison metrics of selected corresponding nodes from each PTM. In such embodiments, aligning the reference PTM and the target PTM comprises inserting one or more nodes in proximity of the selected nodes in one of the reference PTM and the target PTM based on the comparison metrics of the selected nodes.

In certain embodiments, the systems may further include a cluster analyzer. The cluster analyzer may be configured to select a subsection of one of the reference PTM and target PTM, and analyze peak information of a plurality of nodes in the subsection. In response to determining one or more nodes having lower peaks in proximity to at least one node having a higher peak, the cluster analyzer may be configured to generate a clustered node combining the nodes having the lower peaks and the at least one node having the higher peak.

BRIEF DESCRIPTION OF THE FIGURES

The patent or application file contains at least one drawing executed in color. Copies of this patent or patent application publication with color drawing(s) will be provided by the Office upon request and payment of the necessary fee. The foregoing and other objects and advantages of the systems and methods described herein will be appreciated more fully from the following further description thereof, with reference to the accompanying drawings wherein:

FIG. 3 depicts a block diagram for an illustrative embodiment of a peak topography map (PTM) Generator;

FIGS. 15A-15C depict illustrative topography partitions for an oil sample; and

DETAILED DESCRIPTION

Figure 1:
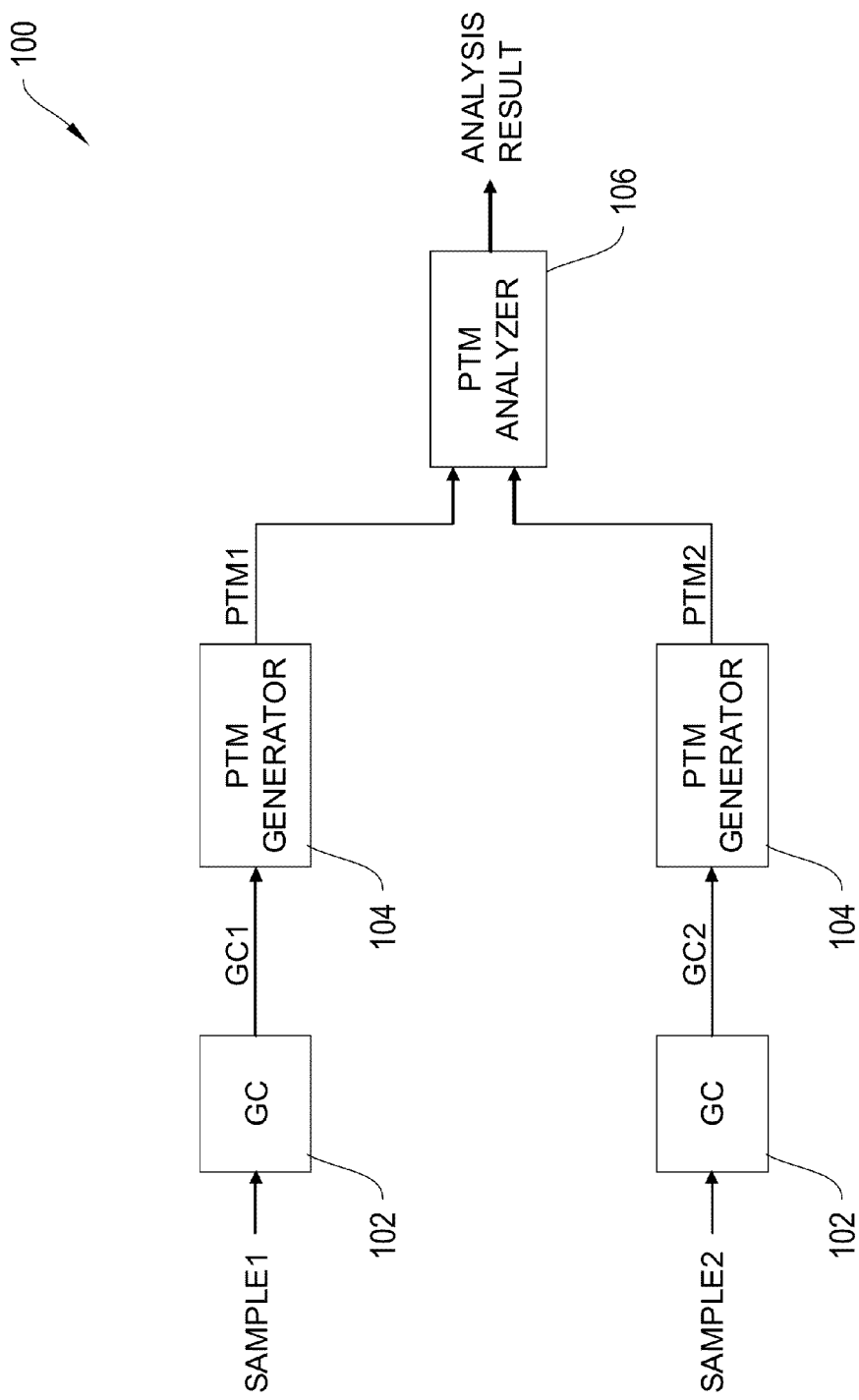
FIG. 1 depicts a block diagram for an illustrative embodiment of a topographic analysis system.

To provide an overall understanding of the systems and methods described herein, certain illustrative embodiments will now be described, including systems and methods for topographic analysis of one or more samples. However, it will be understood by one of ordinary skill in the art that the systems and methods described herein may be adapted and modified for other suitable applications and that such other additions and modifications will not depart from the scope thereof.

Two-dimensional gas chromatography (GC×GC) provides detailed information for analyzing molecular mixtures such as crude petroleum that lies largely uninterpreted in traditional chromatographic analysis. Though GC×GC is technically mature from a hardware perspective, there remain challenges in the interpretation of the detailed information on the chemical compounds provided by the high-resolution images it generates. Classifying the highly detailed information inherent in the GC×GC images into separable components that provide valuable insight into the inner structure, distribution, origin and history of the chemical mixture is an open signal processing challenge. Traditional classification techniques are not suited for this purpose as they rely on template or texture matching in some form or the other, and choice of the right template to match against is often the open question to chemists. Therefore, GC×GC image analysis presents both a daunting problem to the chemist and an exciting challenge to the signal processing community.

The systems and methods described herein can separate strongly correlated signatures on a GC×GC chromatogram and provide a quantitative measure for classifying petroleum hydrocarbons to different sources of oil. While there is universal agreement that hydrocarbon signatures define crude petroleum itself, there is little consensus on how to exploit the smaller variations between these signatures to map an oil sample to a distinct source. Current techniques include measuring peak ratios of carefully selected biomarkers to distinguish between oil samples, but such peak-ratio analysis at best provides a semi-quantitative measure for comparing two oil samples and deciding whether they come from distinct sources. The combination of chromatographic variability, strong correlation between the major signature components, and lack of sophisticated statistical techniques linking nuances between hydrocarbon signatures and hydrocarbon sources make a compelling case for developing signal processing techniques targeted for precise chemical fingerprinting of petroleum hydrocarbons.

The systems and methods described herein include a topographic analysis system that can extract crucial information from a (GC×GC) image in a way that is independent of chromatographic variability, and provides a quantitative basis for deriving and comparing chemical signatures. Using this topography mapping, the systems and methods described herein may separate oil samples based on their origin, and may even mathematically isolate which compounds in the samples may hold the key to their respective fingerprinting. Such scientific insights on chemical fingerprinting of petroleum hydrocarbons have been typically difficult to derive using traditional techniques.

Figure 16:
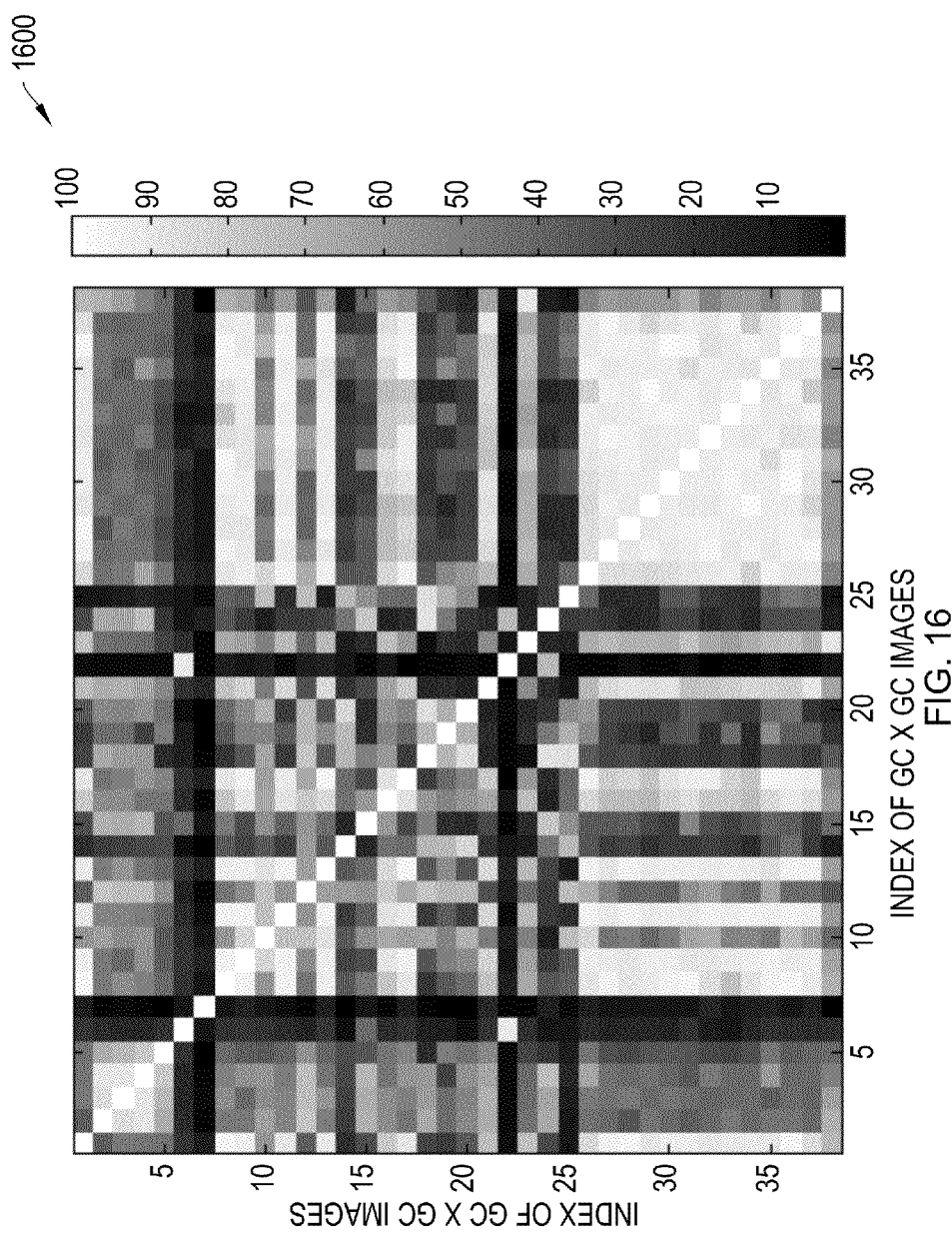
FIG. 16 depicts an illustrative comparison matrix between 38 oil samples.

In the following passages, an illustrative topographic analysis system and an illustrative computer system for executing topographic analysis of one or more samples is described with reference to FIG. 1 and FIG. 2, respectively. Further illustrative embodiments of components of a topographic analysis system including a PTM Generator and a PTM Analyzer are described with reference to FIGS. 5-10 and FIGS. 11-14B, respectively. In particular, a topographic analysis system that performs topography partitioning of samples is described with reference to FIGS. 13-14B. Finally, FIGS. 15A-16 depict illustrative analysis results from a topographic analysis system including illustrative topography partitions for an oil sample and an illustrative comparison matrix between 38 analyzed oil samples.

Figure 2:
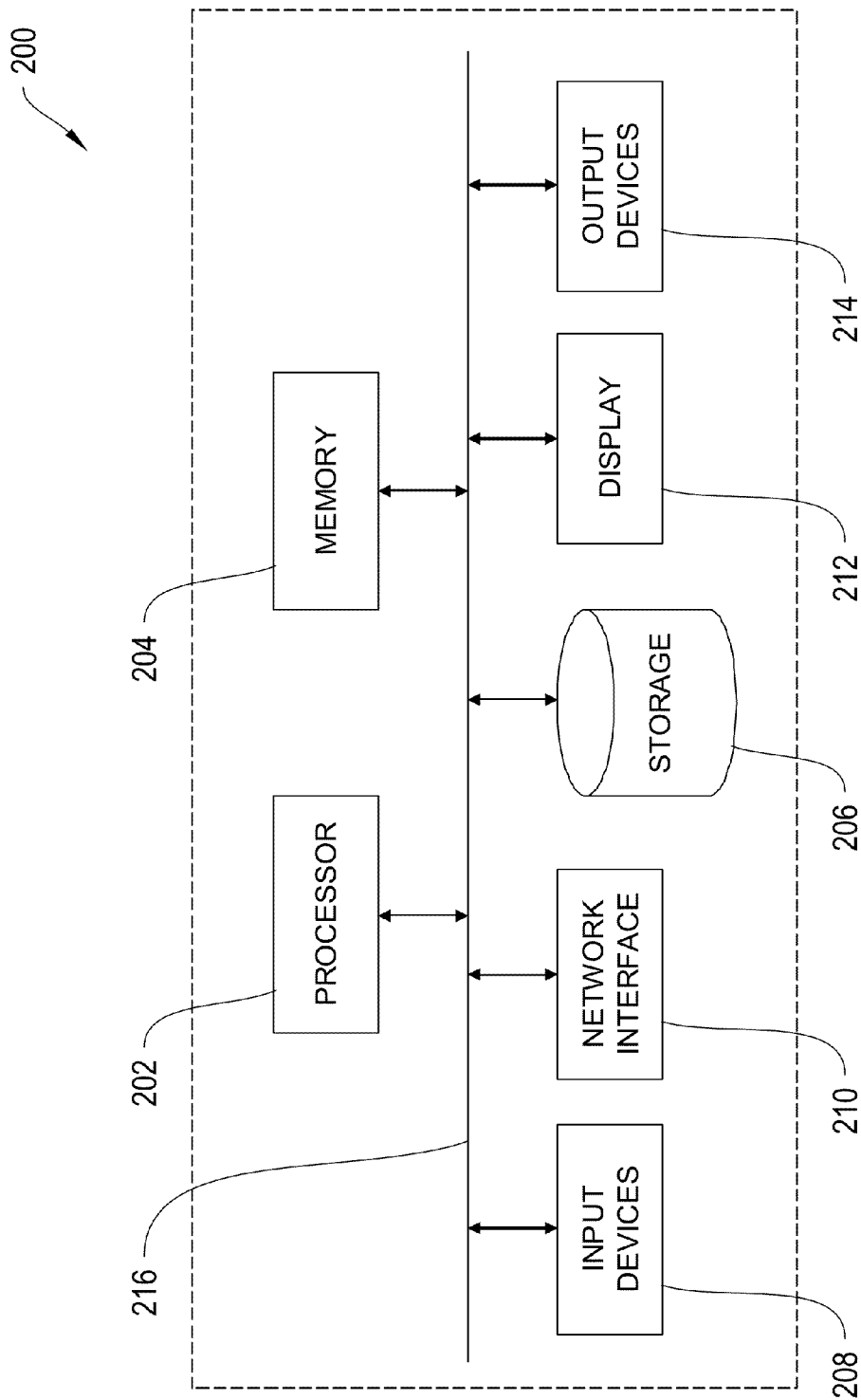
FIG. 2 depicts a block diagram for an illustrative computer system for executing topographic analysis of one or more samples.

FIG. 1 depicts a block diagram for an illustrative embodiment of a topographic analysis system 100. System 100 include GC×GC image generators 102, PTM Generators 104, and PTM Analyzer 106. Alternative embodiments of system 100 may include more or fewer GC×GC image generators or PTM Generators. The GC×GC image generators 102 receive samples and generate representative GC×GC images or datasets for the samples. For example, a GC×GC image generator may be an AGILENT 7890A gas chromatograph or an AGILENT 6890N gas chromatograph, both manufactured by AGILENT TECHNOLOGIES of Wilmington, Del. The GC×GC datasets are passed on to PTM Generators 104 that generate peak topography maps (PTMs) for the respective samples, which are then compared using the PTM Analyzer 106 to deliver the required analysis results.

One or more components, in any suitable combination, of the topographic analysis system 100 may be implemented on a computer processing system. FIG. 2 depicts a block diagram for an illustrative computer system 200 for executing Topographic analysis of one or more samples. System 200 includes processor 202, memory 204, storage devices 206, input devices 208, network interface 210, display device 212, and output devices 214. The system components may be in communication via interconnect bus 216. Processor 202 may be from microprocessor series such as Intel Pentium, Intel Core, Intel Core 2, Intel Xeon, AMD Athlon, AMD Phenom, IBM Power, IBM PowerPC, or other such microprocessor series. Processor 202 may include a single microprocessor or a plurality of microprocessors for configuring system 200 as a multi-processor system. Memory 204 may include read-only (ROM) or random access (RAM) memories, such as a synchronous dynamic random access memory (SDRAM), capable of storing data as well as instructions to be executed by processor 202.

Storage 206 may include a hard disk drive (HDD), a tape drive, a flash drive, a floppy drive, a compact disc (CD), a digital versatile disc (DVD), or other suitable fixed or movable computer readable media, for storing data and instructions for use by the Processor 202. Input devices 208 may include a keyboard, a mouse, a trackball, or other suitable devices. Network interface 210 may include a network card, a modem, a serial port, a bus adapter, or any other suitable data communications device for communicating with one or more local or remote systems. System 200 may communicate over a network through the network interface 210. The network may be an optical network, a wired network, a wireless network (e.g., satellite or cellular network), or any other suitable type of network. Display 212 may include one or more liquid crystal display (LCD) or cathode ray tube (CRT) monitors, or other suitable devices. Output devices 214 may include a projector, a printer, speakers, or other such devices. A portion of the topographic analysis system 100 may be implemented by processor 202 in conjunction with other components of system 200.

Generally, the methods described herein may be executed on a conventional data processing platform such as an IBM PC-compatible computer running the Windows operating systems, a SUN workstation running a UNIX operating system or another equivalent personal computer or workstation. Alternatively, the data processing system may comprise a dedicated processing system that includes an embedded programmable data processing unit.

Certain of the processes described herein may also be realized as one or more software components operating on a conventional data processing system such as a UNIX workstation. In such embodiments, the processes may be implemented as a computer program written in any of several languages well-known to those of ordinary skill in the art, such as (but not limited to) C, C++, FORTRAN, Java or BASIC. The processes may also be executed on commonly available clusters of processors, such as Western Scientific Linux clusters, which may allow parallel execution of all or some of the steps in the process.

Certain of the methods described herein may be performed in either hardware, software, or any combination thereof, as those terms are currently known in the art. In particular, these methods may be carried out by software, firmware, or microcode operating on a computer or computers of any type, including pre-existing or already-installed image processing facilities capable of supporting any or all of the processor's functions. Additionally, software embodying these methods may comprise computer instructions in any form (e.g., source code, object code, interpreted code, etc.) stored in any computer-readable medium (e.g., ROM, RAM, magnetic media, punched tape or card, compact disc (CD) in any form, DVD, etc.). Furthermore, such software may also be in the form of a computer data signal embodied in a carrier wave, such as that found within the well-known Web pages transferred among devices connected to the Internet. Accordingly, these methods and systems are not limited to any particular platform, unless specifically stated otherwise in the present disclosure.

FIG. 3 depicts a block diagram for an illustrative peak topography map (PTM) generator 300. The PTM Generator may be implemented on a computer system, e.g., system 200 of FIG. 2, according to illustrative flow diagram 700 of FIG. 7. The PTM representation of a chromatography image, e.g., GC×GC image or dataset, is a feature representation that characterizes the peak information across the entire topography of a GC×GC image into a connected map of peak values. To construct the PTM feature representation of a GC×GC image, the image is first passed through Region Selector 302. Region Selector 302 selects a region or a portion of the GC×GC image for further analysis based on user input, preset instructions, and/or any other suitable input. For example, Region Selector 302 may select a region of a GC×GC image of an oil sample that corresponds to biomarker compounds such as hopanes and steranes. Biomarker compounds like hopanes and steranes are robust and resist environmental weathering. They are therefore important compound groups for fingerprinting oil samples back to their source regardless of potential differences between them due to environmental degradation. Region Selector 302 passes the selected region to Peak Analyzer 304. Peak Analyzer 304 isolates all or substantially all of the peaks in the GC×GC image by employing a peak searching technique, e.g., a gradient-based search. The gradient-based search may include calculating the gradient along the second (vertical) dimension for each point in the first (horizontal) dimension of the GC×GC and isolating the local maxima that represent the peaks of the various compounds along the vertical line. In some embodiments, Peak Analyzer 304 uses any suitable local maxima search. For example, gradient-based search may be modified to identify peaks based on a threshold measure of peak height by width ratio. If this threshold is set high, the identified peaks may only include distinct well-formed peaks and leave ill-formed "blunt" peaks. If this threshold is set high, the identified peaks may only include distinct well-formed as well as minor peaks. In some embodiments, Peak Analyzer 304 performs joint isolation of maxima along both dimensions. Subsequently, each pulse shape or peak in the two-dimensional GC×GC image collapses into a single point representing the peak information, including the peak value, along with the peak location, the peak volume, and/or the order in which the peaks appear (order of elution in the vertical dimension) is preserved in the feature representation. The peak information is then passed onto Matrix Generator 306.

In some embodiments, the peaks are ordered in increasing number of peak locations along the vertical dimension for a given point along the horizontal dimension. In some embodiments, the peak information is normalized against the maximum value of the respective peaks to avoid any unpredictable biases on the overall gain of the GC×GC image. Each PTM node may store peak information including peak value, peak location, peak volume, order of elution in the vertical dimension, and any other suitable information regarding the peak. The [m, n]-th node of the PTM may store the peak information for the $m^{th}$ peak along the vertical direction for the $n^{th}$ point on the horizontal dimension. Matrix Generator 306 may generate this PTM representation of a GC×GC image as a two-dimensional matrix, with N columns and M rows, where the [m, n]-th element represents the corresponding node of the PTM. The number of columns N represents the total number of points along the horizontal dimension of the GC×GC image. In such embodiments, the number of rows M represents the maximum number of peaks, denoted as $p_{max}$, along the vertical dimension for all the n=1, ..., N horizontal points across the entire GC×GC image. The columns that have fewer peaks than M, store the nodes in ascending order of peak locations, and populate the remaining entries of the column with zeros to denote absence of a peak in those nodes for the given PTM. Such entries in the PTM which do not have a peak may be termed "blank" nodes. As will be discussed further below, insertion or deletion of blank nodes to align PTMs is an important part of comparing between samples or comparing an unknown sample to an established source fingerprint. The alignment helps ensure that the same compound gets compared between two PTMs independent of any chromatographic variability shifting the peak locations in the GC×GC images under consideration.

Figure 4A:
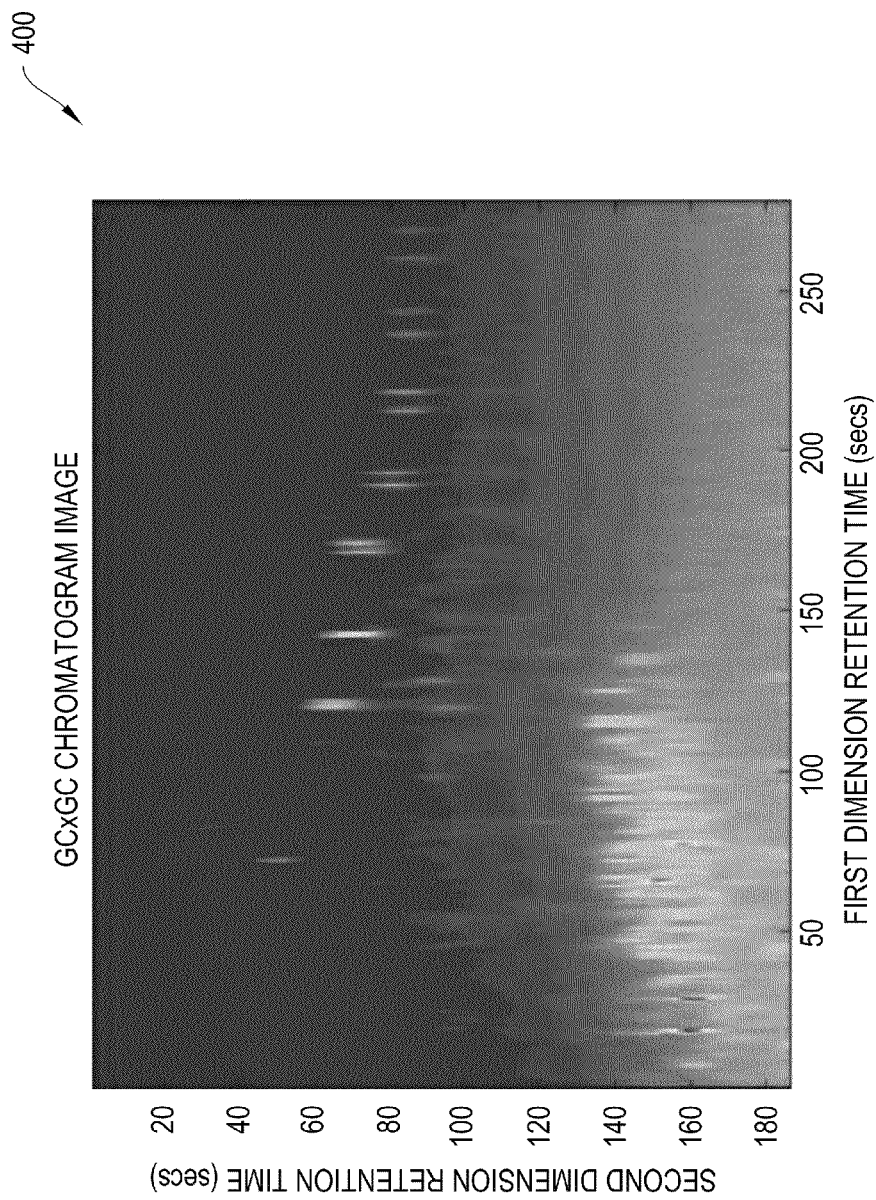
FIG. 4 depicts an illustrative GC×GC chromatography image for an oil sample.

FIG. 4A depicts an illustrative GC×GC chromatography image 400 for a sample. GC×GC data results in two-dimensional separations that provide an order of magnitude in resolution and signal/noise. The horizontal axis represents first dimension retention times, and the vertical axis represents second dimension retention times. GC×GC topography includes all or substantially all peaks—major peaks attributed to well-known major compounds and hundreds of smaller peaks attributed to other minor compounds, which occur in relatively smaller amounts. Such peaks are identified as the lighter portions of the GC×GC image. Traditional chemometric interpretation limits analysis to compounds of known identity that occur in relatively high amounts in a complex mixture like crude oil, and as such, fails to provide collective interpretation of the hundreds, sometimes thousands, of compounds that constitute the GC×GC topography. The compounds which manifest as the well-identified major peaks in a GC×GC image are referred to as the major compounds. However, GC×GC topography also consists of hundreds of smaller peaks attributed to other compounds, referred to as the minor compounds, which occur in relatively smaller amounts. Traditionally, the impact of minor compounds, which are typically difficult to identify accurately, is ignored in chemometric analysis; even though they collectively contribute to the majority of GC×GC topography. Therefore, limiting chemometric interpretation to the major compounds fails to interpret the collective impact of GC×GC topography and unlock hitherto unknown insights that are available in highly detailed GC×GC separations of hundreds, sometimes thousands, of compounds. For example, biomarkers like hopanes and steranes are robust and resist environmental weathering. They are therefore important compound groups for fingerprinting oil samples back to their source regardless of potential differences between them due to environmental degradation. In some embodiments, analysis of GC×GC images includes selecting a region or portion of the GC×GC image corresponding to important compound groups, such as hopanes and steranes, in order to better interpret the available data.

Figure 4B:
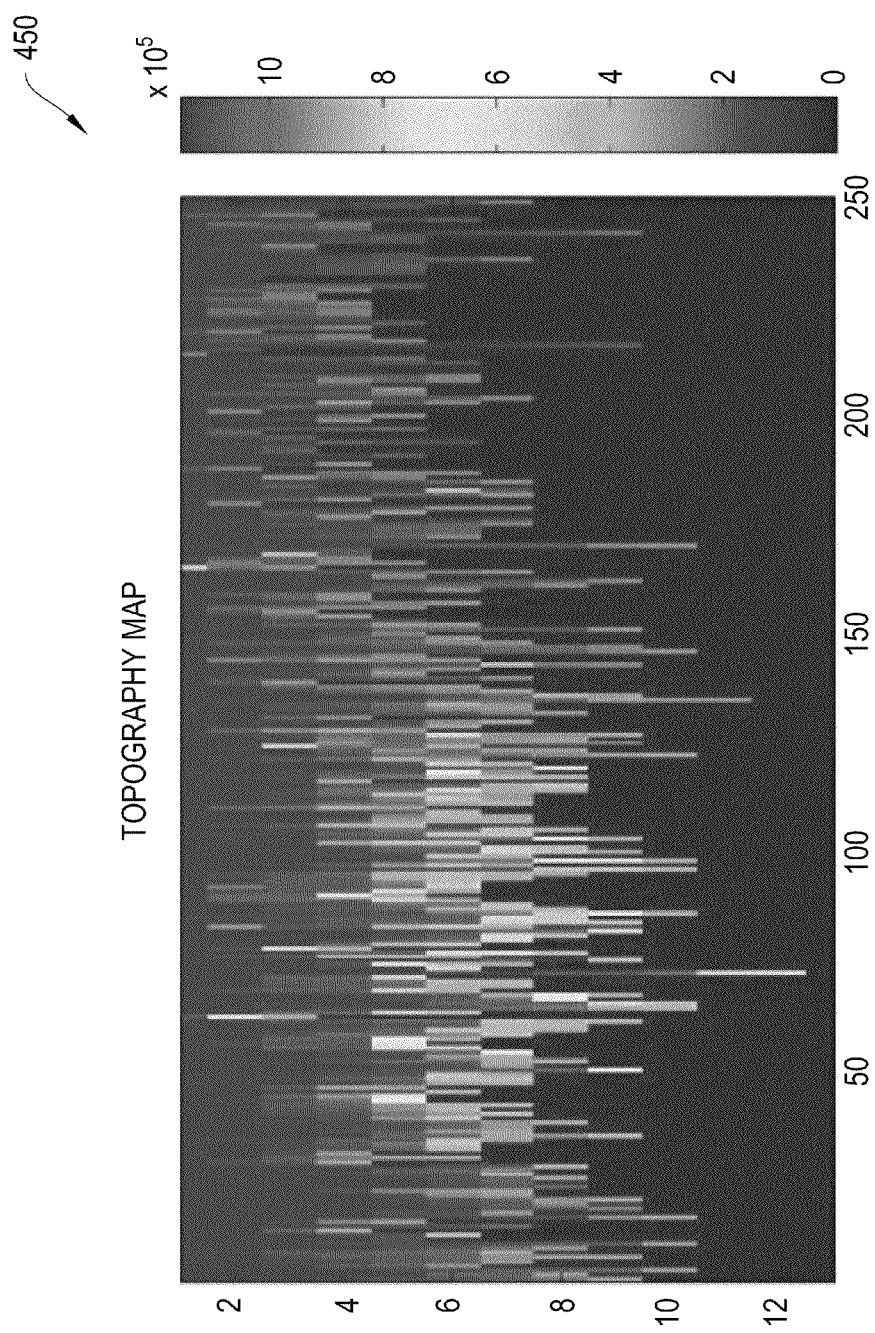

FIG. 4B depicts an illustrative PTM 450 for the GC×GC chromatography image 400 of FIG. 4A. The PTM may be generated by Matrix Generator 306, and the illustrative example of FIG. 4B shows a visual representation of such a generated PTM. Assuming x-y axes, the point (x,y) in the PTM shows the peak value (lighter color corresponding to higher value) for the $y^{th}$ peak along the vertical direction of a GC×GC image for the $x^{th}$ point on the horizontal dimension of the GC×GC image. The topographic analysis system 100 of FIG. 1 locates the peak values of all peaks in the GC×GC dataset and stores the peak values, preserving, among other things, the relative proximity of the peaks along the vertical direction as they occur in the GC×GC dataset. The PTM is visibly more compressed dataset containing the critical information (peak values, proximity, etc.) of the original GC×GC dataset. Thus, the GC×GC image 400 may be succinctly represented by the two-dimensional PTM matrix with the relevant relational information between compounds preserved without information loss. By construction, the PTM may be relatively immune to chromatographic variability because it considers order rather than the exact peak location to represent compounds. Some alignment between PTMs may be necessary to ensure fair comparison against samples analyzed under significantly diverse conditions. Nonetheless, the PTM may enable broad feature representation of the entire molecular mixture, and may be used as a comprehensive representation of a given petroleum source that is relatively immune to variability. Furthermore, the compact structure of the PTM may lend itself to faster comparison between featured representation of different samples.

Figure 5A:
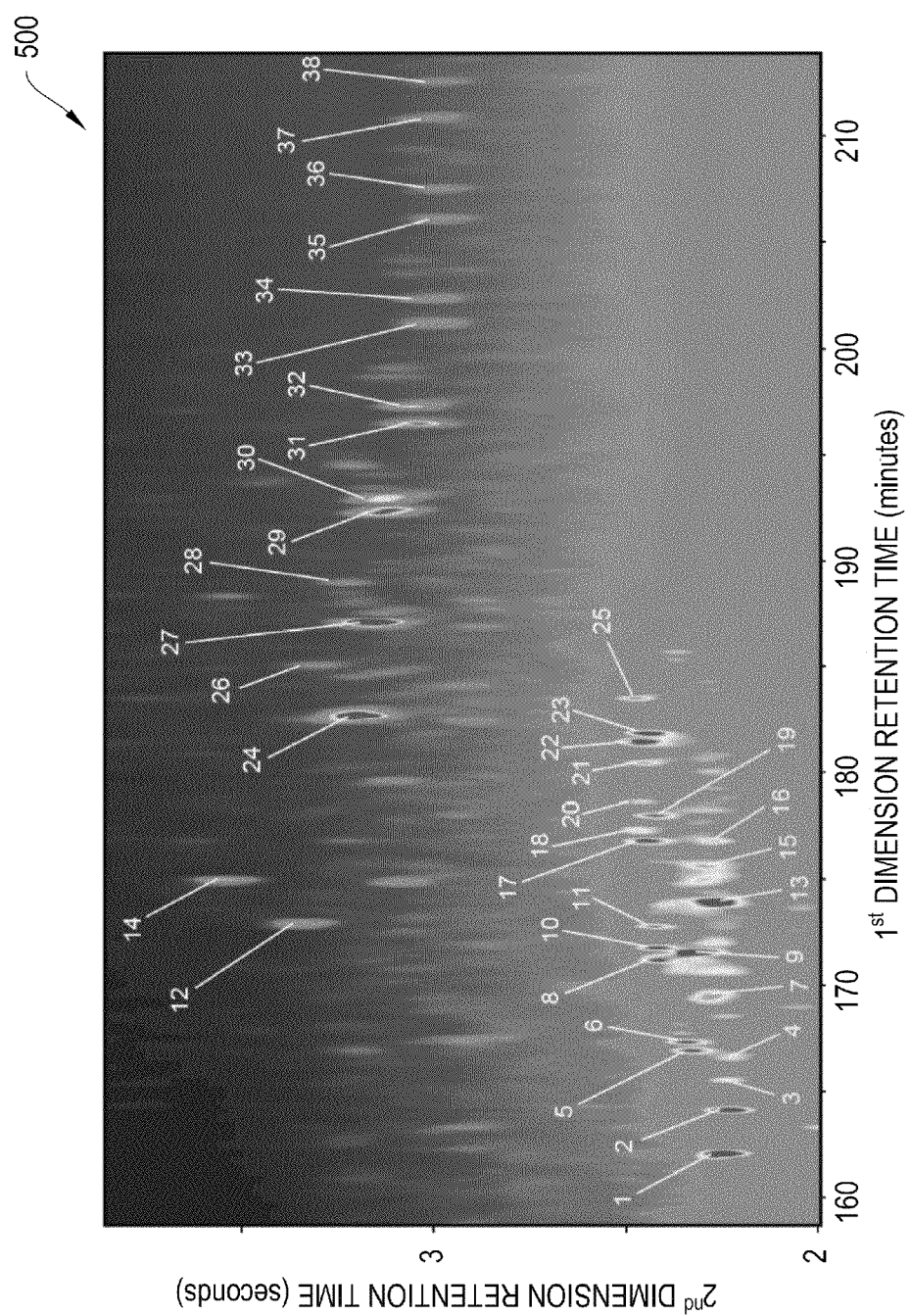
FIG. 5 depicts an illustrative plot of peak shapes and peak values for the GC×GC chromatography image of FIG. 4.

FIG. 5A depicts another illustrative GC×GC chromatography image 500 for a sample. The horizontal axis represents first dimension retention times, and the vertical axis represents second dimension retention times. Traditional chemometric analysis of GC×GC images typically limits interpretation of this rich information to compounds of known identity that occur in relatively high amounts in a complex mixture. These major compounds manifest as the well-identified major peaks in a GC×GC image. However, GC×GC topography also consists of hundreds of smaller peaks attributed to other minor compounds, which occur in relatively smaller amounts. GC×GC topography includes all or substantially all peaks—major peaks attributed to well-known major compounds and hundreds of smaller peaks attributed to other minor compounds, which occur in relatively smaller amounts. Such peaks are identified as the lighter portions of the GC×GC image. The major compounds, which are typically the only compounds considered in traditional interpretation, are identified numerically in FIGS. 5A and 5B as the major peaks, and listed numerically in Table 1 below (with details on the abbreviations and component names). However, we note besides these major peaks that there is significant topographic contribution from many smaller peaks, as evident from the unlabeled peaks in the GC×GC image. These minor peaks, which attain smaller heights and challenging to identify, represent the minor compounds within GC×GC image topography that are typically ignored in traditional chemometric interpretation.

TABLE 1

Figure 5B:
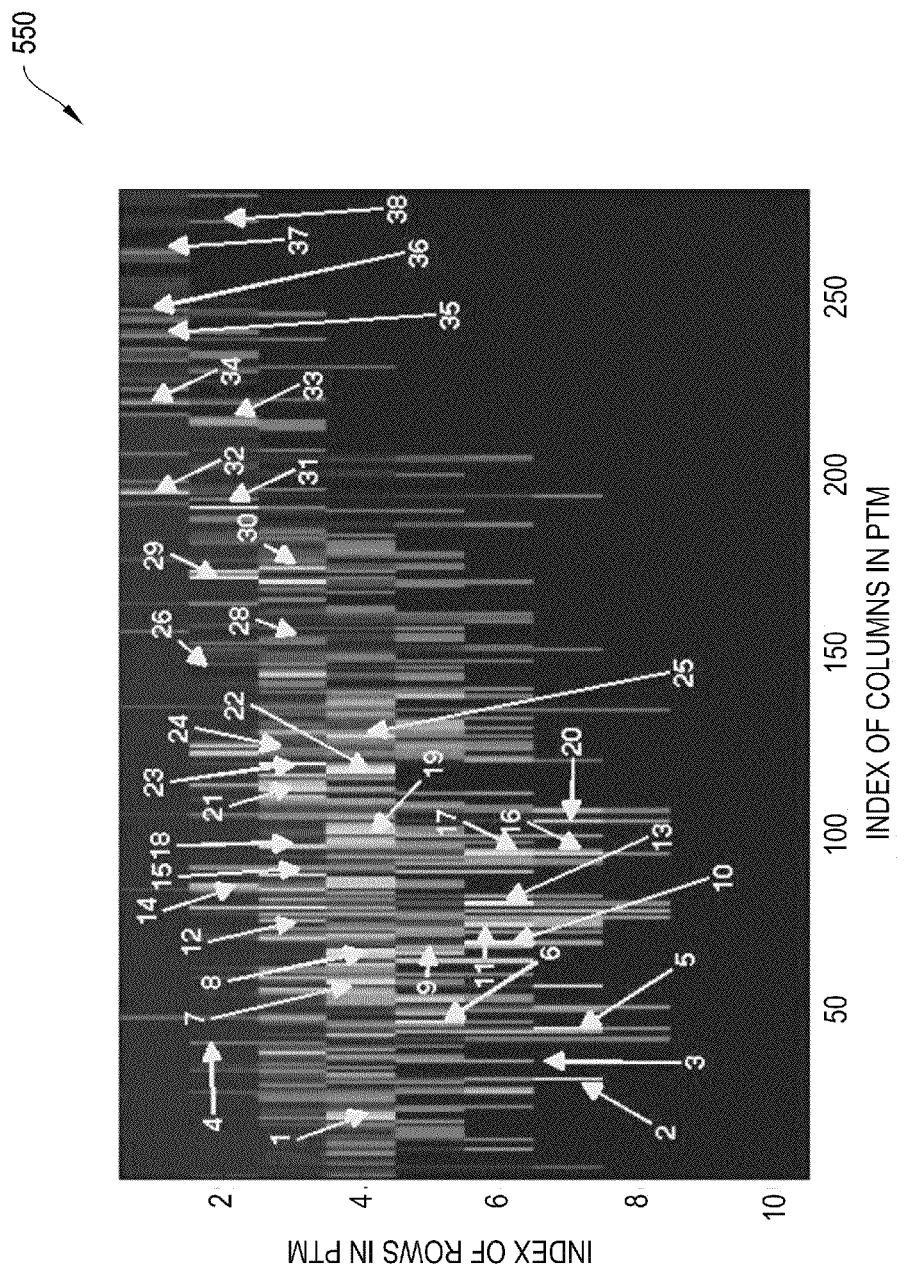

List of compounds labeled in FIGS. 5A-5B

| # | Abbreviation | Component name |
|---|---|---|
| 1 | DiaC27Ba-20S | 13β(H),17α(H)-20S-diacholestane |
| 2 | DiaC27Ba-20R | 13β(H),17α(H)-20R-diacholestane |
| 3 | DiaC27aB-20S | 13α(H),17β(H)-20S-diacholestane |
| 4 | DiaC27aB-20R | 13α(H),17β(H)-20R-diacholestane |
| 5 | DiaC28Ba-20S(24X) | 24X-methyl-13β(H),17α(H)-20S-diacholestane |
| 6 | DiaC28Ba-20S(24Y) | 24Y-methyl-13β(H),17α(H)-20S-diacholestane |
| 7 | DiaC28Ba-20R(24S&R) | 24S&R-methyl-13β(H),17α(H)-20R-diacholestane |
| 8 | C27aBB-20R | 5α(H),14β(H),17β(H)-20R-cholestane |
| 9 | DiaC29Ba-20S(24S&R) | 24S&R-ethyl-13β(H),17α(H)-20S-diacholestane |
| 10 | C27aBB-20S | 5α(H),14β(H),17β(H)-20S-cholestane |
| 11 | C27aaa-20R | 5α(H),14α(H),17α(H)-20R-cholestane |
| 12 | Ts | 18α(H)-22,29,30-trinorneohopane |
| 13 | DiaC29Ba-20R(24S&R) | 24S&R-methyl-13α(H),17β(H)-20R-diacholestane |
| 14 | Tm | 17α(H)-22,29,30-trinorhopane |
| 15 | DiaC29aB-20S(24S&R) | 24S&R-ethyl-13α(H),17β(H)-20S-diacholestane |
| 16 | DiaC29aB-20R(24S&R) | 24S&R-ethyl-13α(H),17β(H)-20R-diacholestane |
| 17 | C28aBB-20R | 24-methyl-5α(H),14β(H),17β(H)-20R-cholestane |
| 18 | C28aBB-20S | 24-methyl-5α(H),14β(H),17β(H)-20S-cholestane |
| 19 | Unknown sterane mass 400 (C29) | Unknown sterane mass 400 (C29) |
| 20 | C28aaa-20R | 24-methyl-5α(H),14α(H),17α(H)-20R-cholestane |
| 21 | C29aaa-20S | 24-ethyl-5α(H),14α(H),17α(H)-20S-cholestane |
| 22 | C29aBB-20R | 24-ethyl-5α(H),14β(H),17β(H)-20R-cholestane |
| 23 | C29aBB-20S | 24-ethyl-5α(H),14β(H),17β(H)-20S-cholestane |
| 24 | NH | 17α(H),21β(H)-30-norhopane |
| 25 | C29aaa-20R | 24-ethyl-5α(H),14α(H),17α(H)-20R-cholestane |
| 26 | NM | 17β(H),21α(H)-30-norhopane |
| 27 | H | 17α(H),21β(H)-hopane |
| 28 | M | 17β(H),21α(H)-hopane |
| 29 | HH(S) | 17α(H),21β(H)-22S-homohopane |
| 30 | HH(R) | 17α(H),21β(H)-22R-homohopane |
| 31 | 2HH(S) | 17α(H),21β(H)-22S-bishomohopane |
| 32 | 2HH(R) | 17α(H),21β(H)-22R-bishomohopane |
| 33 | 3HH(S) | 17α(H),21β(H)-22S-trishomohopane |
| 34 | 3HH(R) | 17α(H),21β(H)-22R-trishomohopane |
| 35 | 4HH(S) | 17α(H),21β(H)-22S-tetrakishomohopane |
| 36 | 4HH(R) | 17α(H),21β(H)-22R-tetrakishomohopane |
| 37 | 5HH(S) | 17α(H),21β(H)-22S-pentakishomohopane |
| 38 | 5HH(R) | 17α(H),21β(H)-22R-pentakishomohopane |

FIG. 5B depicts an illustrative PTM 550 for the GC×GC chromatography image 500 of FIG. 5A. The PTM may be generated by Matrix Generator 306, and the illustrative example of FIG. 5B shows a visual representation of such a generated PTM. Assuming x-y axes, the point (x,y) in the PTM shows the peak value (lighter color corresponding to higher value) for the $y^{th}$ peak along the vertical direction of a GC×GC image for the $x^{th}$ point on the horizontal dimension of the GC×GC image. The topographic analysis system 100 of FIG. 1 locates the peak values of all peaks in the GC×GC dataset and stores the peak values, preserving, among other things, the relative proximity of the peaks along the vertical direction as they occur in the GC×GC dataset. To generate the PTM, system 100 isolate all or substantially all the peaks in the GC×GC image of FIG. 5A by employing a peak searching technique, e.g., a gradient-based maxima search. The major compounds, which are typically the only compounds considered in traditional interpretation, are identified numerically in FIGS. 5A and 5B as the major peaks, and listed numerically in Table 1 above (with details on the abbreviations and component names). However, we note besides these major peaks that there is significant topographic contribution from many smaller peaks, as evident from the unlabeled peaks in the PTM. These minor peaks, which attain smaller heights and challenging to identify, represent the minor compounds within GC×GC topography that are ignored in traditional chemoteric interpretation. The PTM is visibly more compressed dataset containing the critical information (peak values, proximity, etc.) of the original GC×GC dataset. Thus, the GC×GC image 500 may be succinctly represented by the two-dimensional PTM matrix with the relevant relational information between compounds preserved without information loss.

Figure 6:
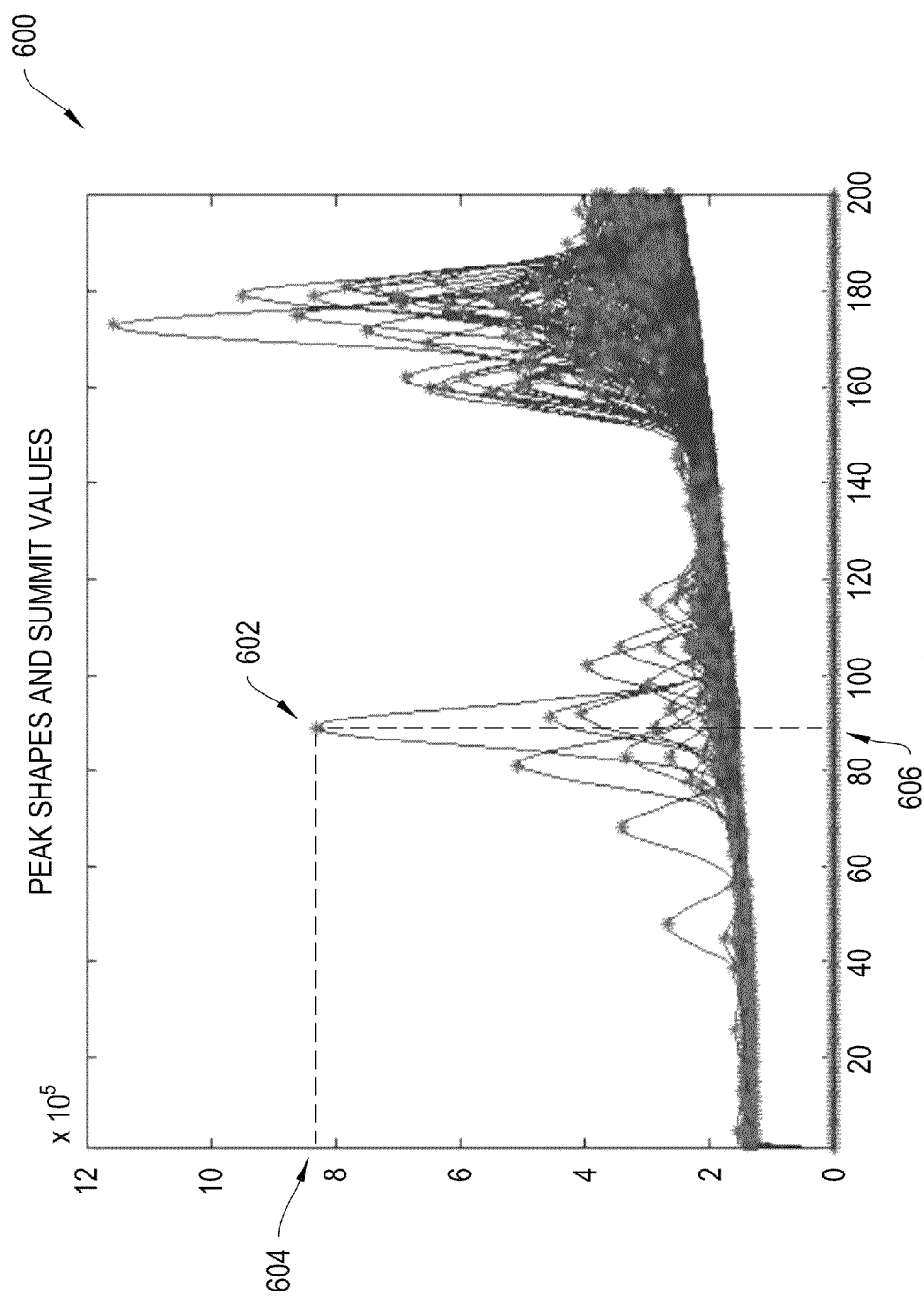
FIG. 6 depicts an illustrative PTM for the GC×GC chromatography image of FIG. 4.

FIG. 6 depicts an illustrative plot 600 of peak shapes and peak values for the GC×GC chromatography image of FIG. 4A. In particular, FIG. 6 shows the peaks isolated (marked with *) over the different peaks along each vertical line in the GC×GC chromatogram in FIG. 4A collapsed onto one plot. The horizontal axis represents second dimension retention times, and the vertical axis represents corresponding peak values. While the bigger or major peaks are easily visible and, therefore, may be isolated manually or by other means, there is a significant contribution to the topology from the many smaller peaks. These smaller or minor peaks are shown as a dense overlap of peaks (marked with *) that are often not accounted for in GC×GC analysis. These minor peaks are analyzed and accounted for by the topographic analysis system at Peak Analyzer 304. Each peak (e.g., 602) has associated peak information including the peak value or height (e.g., 604), along with the peak location (e.g., 606), the peak volume (e.g., area under the curve associated with 602), and/or the order (e.g., n, where 602 is the $n^{th}$ peak).

Figure 7:
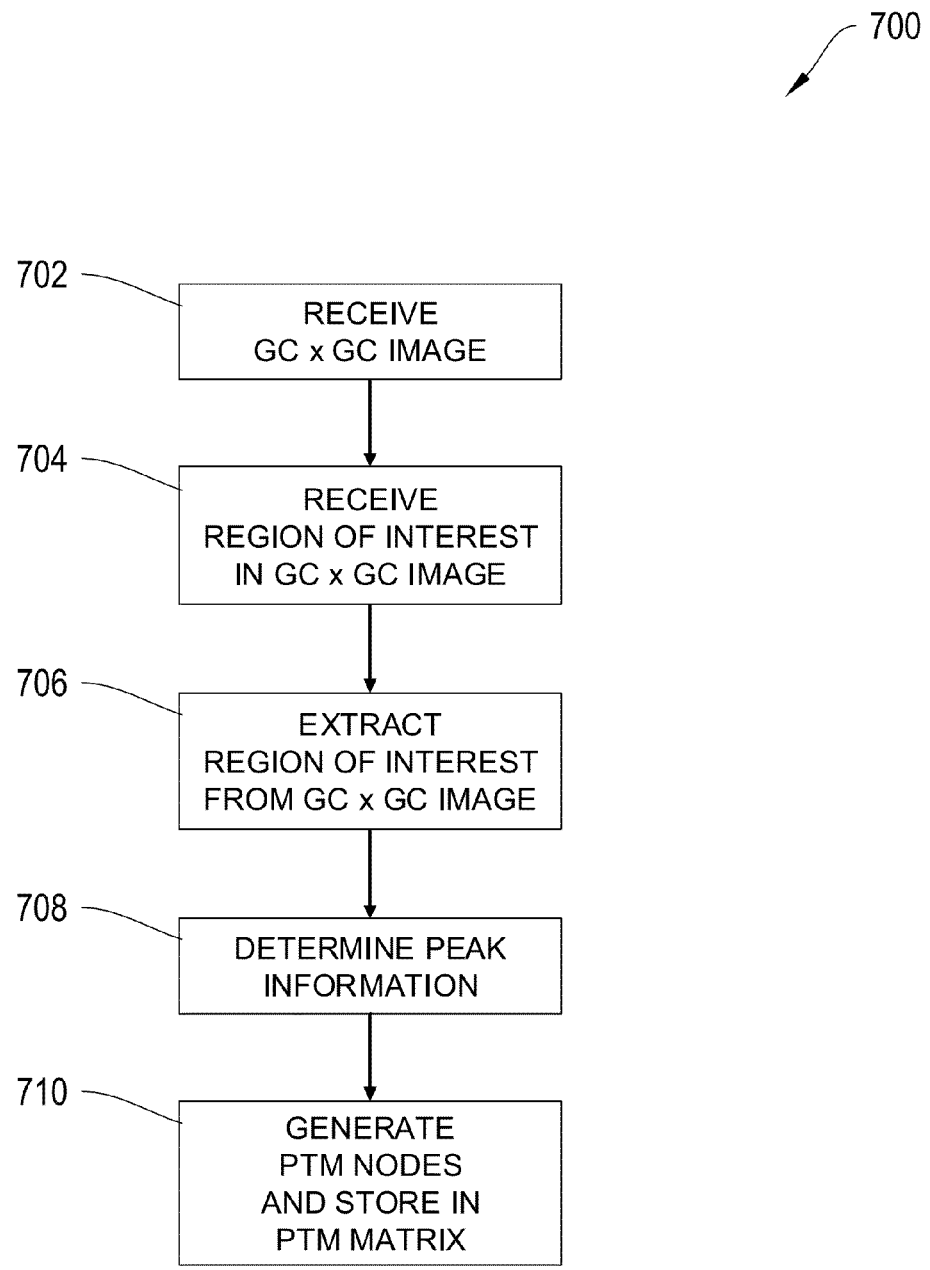
FIG. 7 depicts an illustrative flow diagram for generating a PTM from a GC×GC chromatography image at the PTM Generator of FIG. 7.

FIG. 7 depicts an illustrative flow diagram for generating a PTM from a GC×GC chromatography image at the PTM Generator of FIG. 7. At step 702, PTM Generator 300 receives a GC×GC image (e.g., the GC×GC image of FIG. 4). At step 704, PTM Generator 300 receives a region of interest in the GC×GC image via user input, preset function, or any other suitable input. At step 706, Region Selector 302 of PTM Generator 300 extracts the region of interest from the GC×GC image. At step 708, Peak Analyzer 304 of PTM Generator 300 isolates all the peaks in the GC×GC image (illustrated in e.g., FIG. 5) by employing a peak searching technique, e.g., a gradient-based search. In some embodiments, Peak Analyzer 304 uses any suitable local maxima search. For example, gradient-based search may be modified to identify peaks based on a threshold measure of peak height by width ratio. If this threshold is set high, the identified peaks may only include distinct well-formed peaks and leave ill-formed "blunt" peaks. If this threshold is set high, the identified peaks may only include distinct well-formed as well as minor peaks. At step 710, Matrix Generator 306 of PTM Generator 300 generates the PTM representation of a GC×GC image as a two-dimensional matrix, with N columns and M rows, where the [m, n]-th element represents the corresponding node of the PTM (e.g., PTM 600 of FIG. 6). The [m, n]-th node of the PTM stores the peak value and peak location for the $m^{th}$ peak along the vertical direction for the $n^{th}$ point on the horizontal dimension.

As noted earlier, peaks in a PTM can have various shapes, sizes, and locations. In some embodiments, peaks may be clustered close together. In such embodiments, PTM Generator 300 of FIG. 3 is augmented to further analyze a generated PTM. The further analysis includes analyzing peak information to locate bigger or major peaks having one or more smaller or minor peaks in their proximity. Such peaks in proximity are typically a single peak that has been broken up in the dataset due to the measurement resolution of the GC×GC image generator. For example, a peak that spans 0.3 seconds in retention time in the first dimension of the GC×GC image may be broken up into three peaks if the measurement resolution of the GC×GC image generator is 0.1 seconds. In such a case, the nodes having the major peak and the proximal minor peaks may be clumped or clustered into a single node to generate a clustered PTM. In some embodiments, there may be two or more major peaks and/or one or more minor peaks in proximity that may be considered as candidates for a clumped or clustered node. The threshold for peaks that may be considered proximal, or the "neighborhood" for the peak, may be based on user input, preset instructions, or any other suitable input. In some embodiments, the "neighborhood" for the peak may be defined as a rectangular boundary of nodes, e.g., three vertical nodes by two horizontal nodes.

Figure 8:
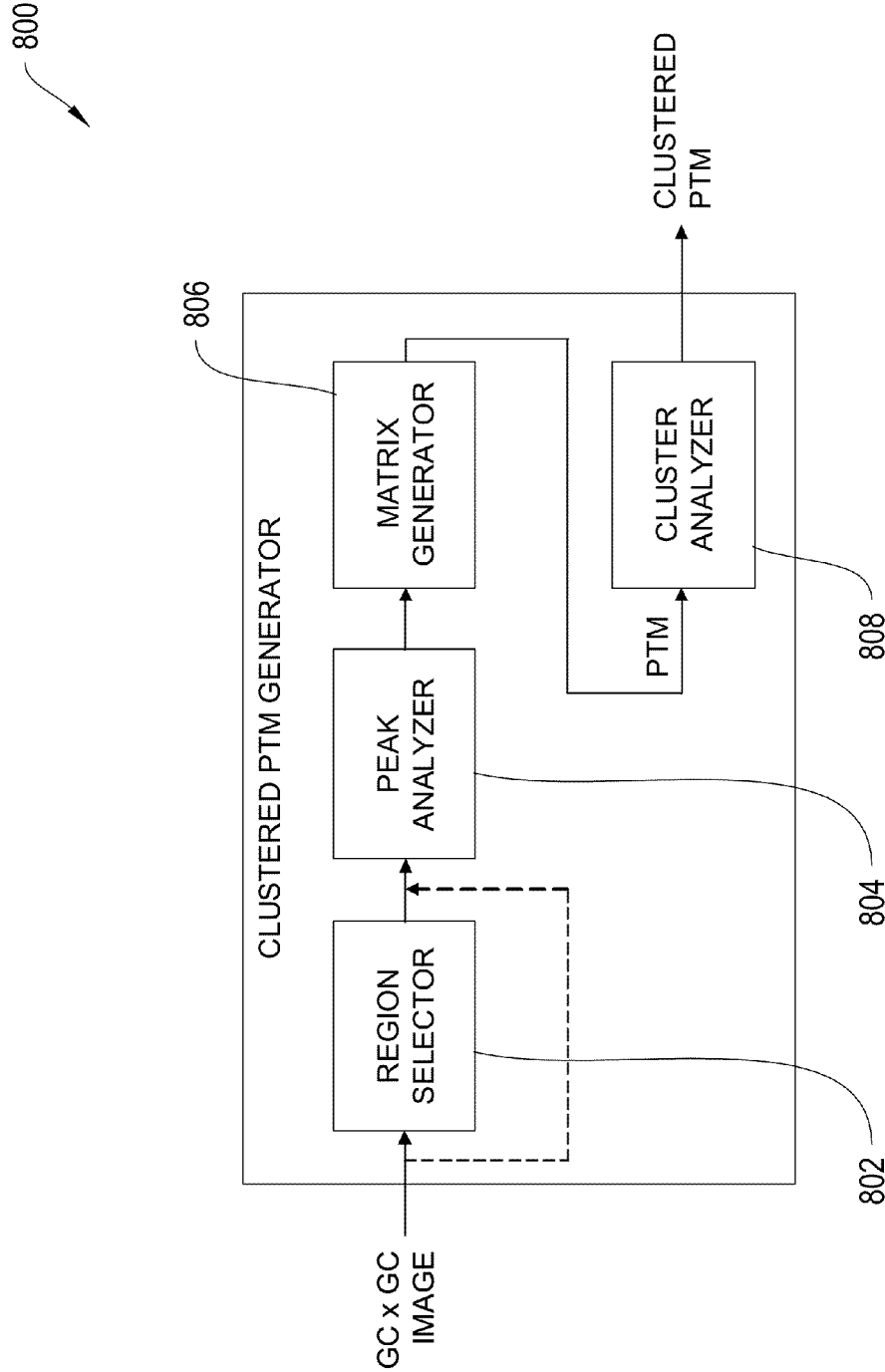
FIG. 8 depicts a block diagram for an illustrative embodiment of a clustered PTM Generator.
Figure 9:
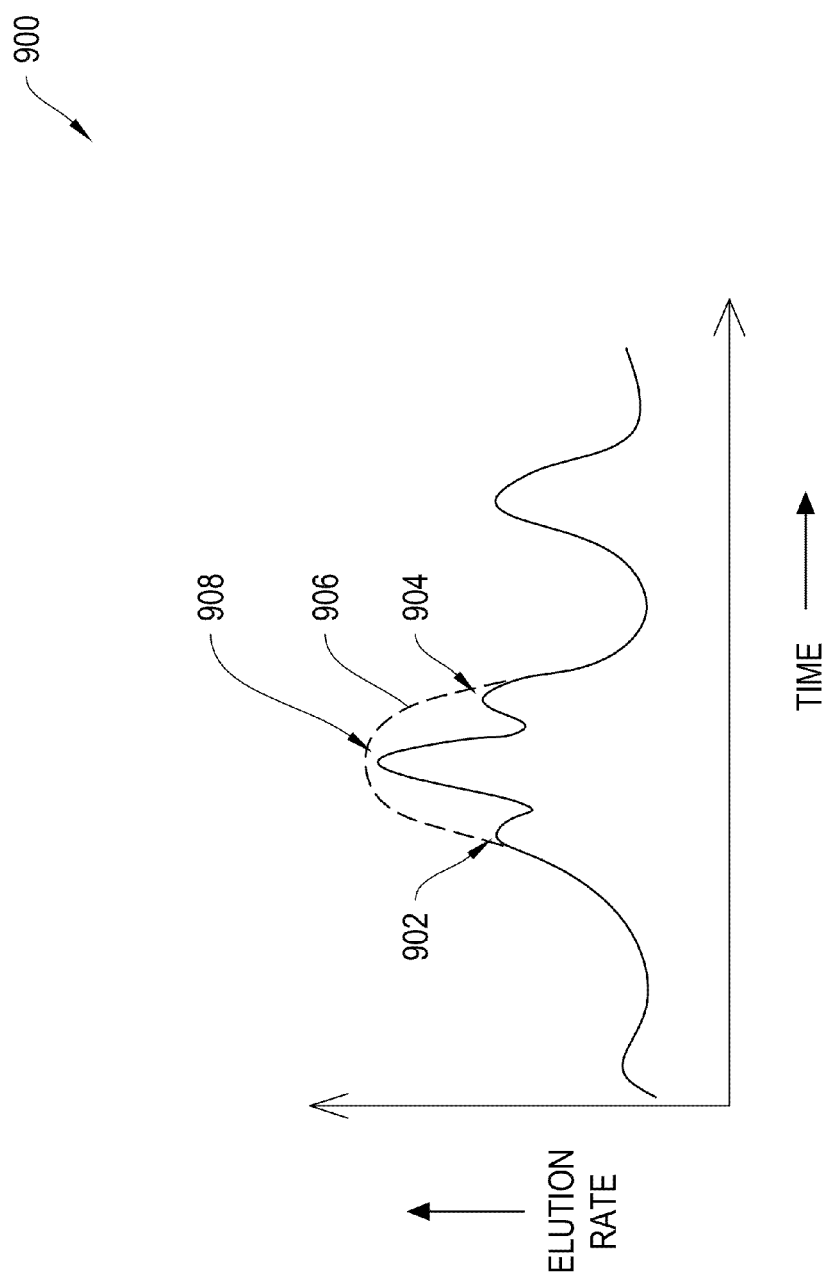
FIG. 9 depicts an illustrative plot showing a suitable candidate for a node in a clustered PTM.

FIG. 8 depicts a block diagram for an illustrative embodiment of a clustered PTM Generator 800. The PTM Generator may be implemented on a computer system, e.g., system 200 of FIG. 2, according to illustrative flow diagram 1000 of FIG. 10. The PTM representation of a chromatography image, e.g., GC×GC image or dataset, is a feature representation that characterizes the peak information across the entire topography of a GC×GC image into a connected map of peak values. To construct the PTM feature representation of a GC×GC image, the image may be first passed through Region Selector 802. Region Selector 802 selects a region of the GC×GC image for further analysis based on user input, preset instructions, or any other suitable input. For example, Region Selector 801 may select a region of a GC×GC image of an oil sample that corresponds to biomarker compounds such as hopanes and steranes. Region Selector 802 passes the selected region to Peak Analyzer 804. Peak Analyzer 804 isolates all the peaks in the GC×GC image by employing a peak searching technique, e.g., a gradient-based search. The gradient-based search includes calculating the gradient along the second (vertical) dimension for each point in the first (horizontal) dimension of the GC×GC and isolating the local maxima that represent the peaks of the various compounds along the vertical line. In some embodiments, Peak Analyzer 804 uses any suitable local maxima search. In some embodiments, Peak Analyzer 804 performs joint isolation of maxima along both dimensions. Subsequently, each pulse shape or peak in the two-dimensional GC×GC image collapses into a single point representing the peak value. Each node in the PTM stores the peak value, along with the peak location, and the order in which the peaks appear is preserved in the feature representation. In some embodiments, the PTM nodes are normalized against the maximum value of the respective peaks to avoid any unpredictable biases on the overall gain of the GC×GC image. The peaks are ordered in increasing number of peak locations along the vertical dimension for a given point along the horizontal dimension. The [m, n]-th node of the PTM stores the peak value and peak location for the $m^{th}$ peak along the vertical direction for the $n^{th}$ point on the horizontal dimension. Matrix Generator 806 generates this PTM representation of a GC×GC image as a two-dimensional matrix, with N columns and M rows, where the [m, n]-th element represents the corresponding node of the PTM. Finally, Cluster Analyzer 808 receives the generated PTM and analyzes the nodes in the PTM for bigger or major peaks having one or more smaller or minor peaks in proximity to the major peak (e.g., as shown in FIG. 9). If such nodes are found, Cluster Analyzer 808 creates a clustered PTM that includes a single node that represents the major and the proximal minor peaks. The single node may include peak value and peak location data for each peak in the clustered node.

FIG. 9 depicts an illustrative plot 900 showing a suitable candidate for a node in a clustered PTM. Plot 900 includes a major peak 908 having minor peaks 902 and 904 located in its proximity. It is likely that that a single peak was broken up into three peaks based on the measurement resolution of the GC×GC image generator. In such a case, the nodes having the major peak 908 and the proximal minor peaks 902 and 904 may be clumped or clustered into a single node for the combined peak 906. The clustered PTM node represents the major and the proximal minor peaks, and may include peak value and peak location data for each peak in the clustered node. The clustered PTM node may include three, four, five, or any other suitable number of peaks. Not all peaks in the PTM need to be clustered. In some cases, even though peaks may be in proximity, their respective nodes may not be clustered and may be kept separate. This is because the Clustered PTM Generator 800 may allow for user-control and adjustment of the proximity parameter based on the application.

Figure 10:
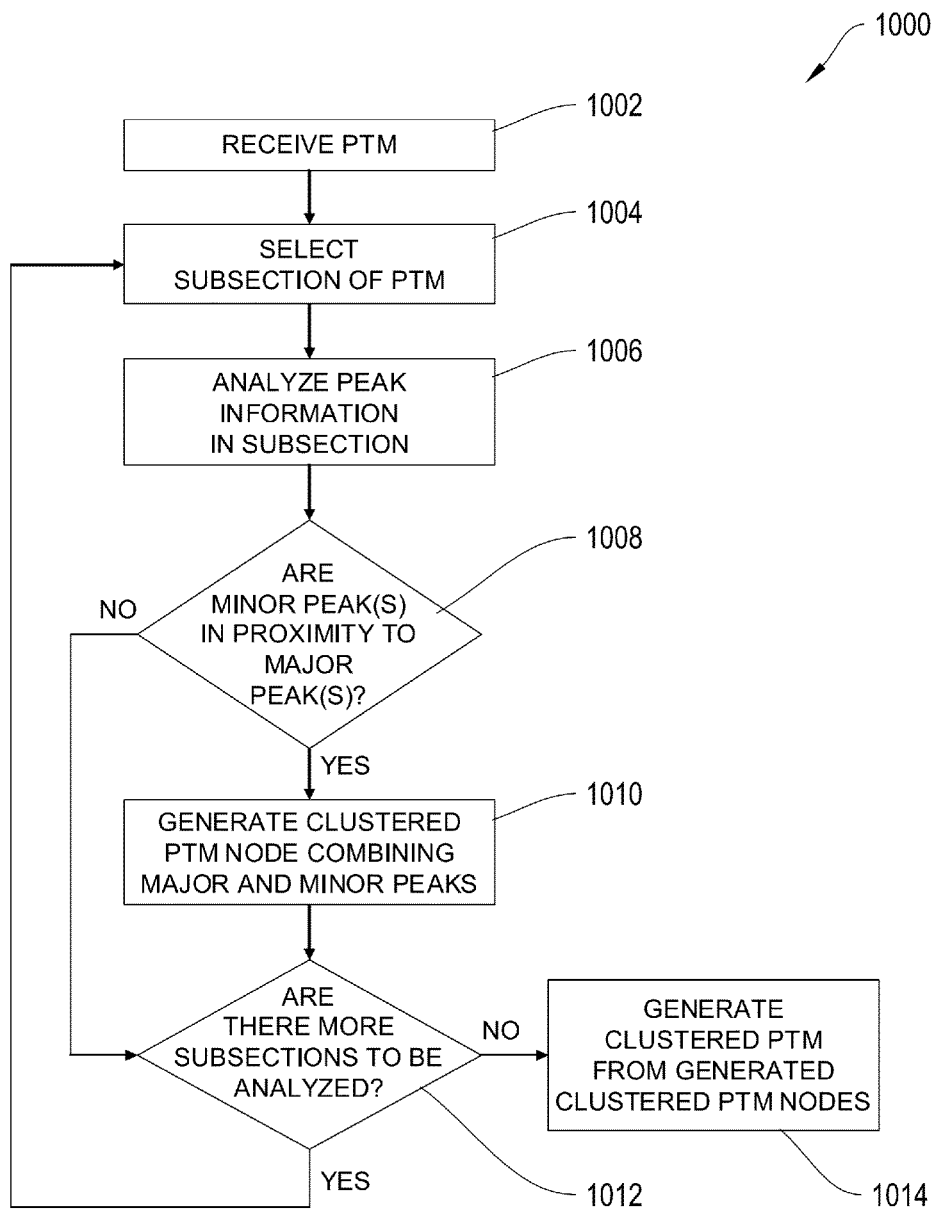
FIG. 10 depicts an illustrative flow diagram for generating a clustered PTM from a PTM at the Cluster Analyzer of the Clustered PTM Generator of FIG. 8.

FIG. 10 depicts an illustrative flow diagram 1000 for generating a clustered PTM from a PTM at the Cluster Analyzer 808 of FIG. 8. The Cluster Analyzer 808 may be implemented on a computer system, e.g., system 200 of FIG. 2. At step 1002, Cluster Analyzer 808 receives the generated PTM (e.g., from Matrix Generator 806). At step 1004, Cluster Analyzer 808 selects a subsection of the PTM to analyze for potential nodes that may be combined. The selection may be based on user input, a preset function, or any other suitable input. At step 1006, Cluster Analyzer 808 analyzes the peak information for the nodes in the subsection. At step 1008, Cluster Analyzer 808 checks whether one or more minor peaks are found proximal to major peak. If not, Cluster Analyzer 808 moves to step 1012. If so, at step 1010, Cluster Analyzer 808 generates a clustered PTM node combining the major peak and the proximal minor peaks. The clustered PTM node represents the major and the proximal minor peaks, and may include peak value and peak location data for each peak in the clustered node. At step 1012, Cluster Analyzer 808 checks whether any subsections of the PTM remain to be analyzed for potential nodes that may be combined. If so, Cluster Analyzer 808 moves to step 1004. If not, Cluster Analyzer 808 generates a clustered PTM having the newly generated clustered PTM nodes.

Figure 11:
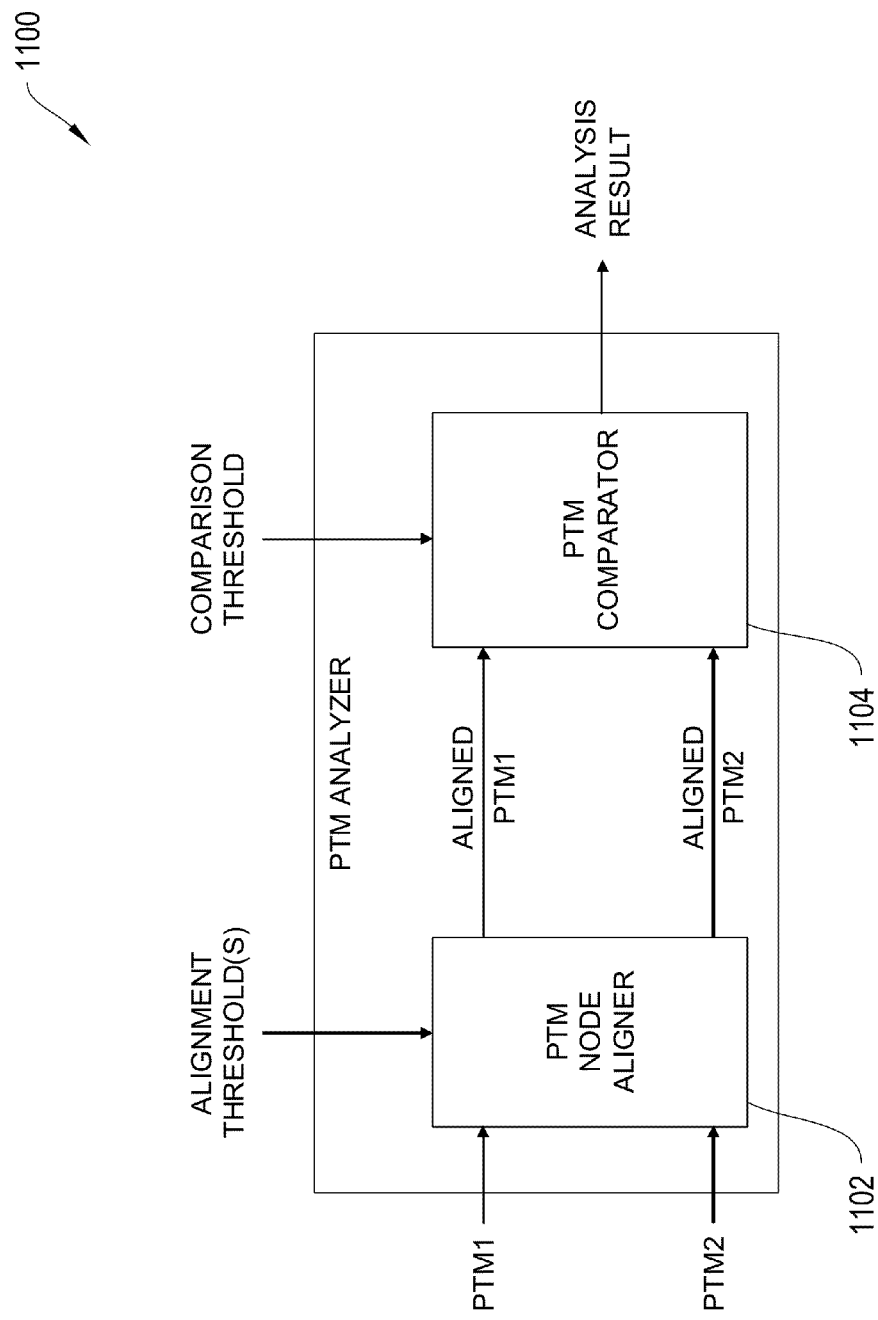
FIG. 11 depicts a block diagram for an illustrative embodiment of a PTM Analyzer.

Once the PTM (or clustered PTM) has been generated, it passes to the PTM Analyzer (e.g., PTM Analyzer 106 of FIG. 1). FIG. 11 depicts a block diagram for an illustrative PTM Analyzer 1100. The PTM Analyzer 1100 may be implemented on a computer system, e.g., system 200 if FIG. 2, according to illustrative flow diagrams 1200 and 1250 of FIGS. 12A-12B. PTM Analyzer 1100 receives two or more PTMs for comparison. PTM Analyzer 1100 passes the PTMs to Node Aligner 1102. As discussed above, a PTM, at each node, may store the value of a peak, peak location and the order in which the peak appears along the second (vertical) direction in a GC×GC image. However, when comparing two PTMs, the respective peaks may be not be aligned. For example, a peak appearing in both PTMs may be at slightly different locations in the respective PTM matrices. So, although these peaks may be referencing the same peak (i.e., the same compound), the PTMs may appear to be different. To alleviate this issue, Node Aligner 1102 processes the two PTMs to match against each other, thereby ensuring that the same compound gets compared between two PTM nodes independent of any chromatographic variability shifting the peak locations in the GC×GC images under consideration. The peak location stored at a given node may vary from sample to sample due to variability, which does not affect peak-to-peak comparisons between samples so long as the order of the node remains the same. However, since the order of the node is critical for peak-to-peak comparisons between samples, it may be important that the nodes between PTMs being compared are aligned to represent the same compounds.

The peak locations, stored at each node, may offer critical side information needed to establish whether the compounds stored at equivalent nodes between two PTMs are indeed the same. This is a measure vulnerable to variability, as a shift between peak locations might indicate different compounds or a shift due to chromatographic variability. In certain embodiments, to ensure peak-to-peak comparisons independent of any chromatograph-induced variability in pulse shape or alignment, Node Aligner 1102 performs the following procedure for node alignment between two PTMs, $P_1$ and $P_2$.

Assuming Θ denotes the maximum deviation in the second or vertical dimension due to chromatographic variability for a given position along the horizontal dimension of the GC×GC image. More generally, Θ may denote a threshold representing the degree to which nodes in $P_1$ and $P_2$ have to be similar or aligned to consider $P_1$ as being aligned to $P_2$. In some embodiments, Θ may be a variability threshold set at maximum deviation between well-known compounds for oil injections, e.g., those based on the compounds listed in Table 1 above. Node Aligner 1102 computes the value of Θ as the maximum deviation between the peaks for well-known compounds over different physical samples and may be set as the expected maximum variability for a gas chromatogram. It can also be computed more locally as the peak spread around a peak value, i.e., $$\Theta[m, n] = \frac{s(r, p[m, n])}{2},$$

where s(r) is the spread under the peak p[m, n] at the [m,n]-th position of the PTM and captures r percent of the total peak volume. For both local and global interpretations of the alignment threshold, Θ may be evaluated statistically as the expected deviation between the same peaks for different runs of the same sample, or between samples whose peak distribution should be very similar as they derive from the same source. Θ may be used as the alignment threshold for the vertical retention time of a given compound and use it as a parameter to sync nodes between two PTMs.

Assuming $\Theta[m,n]=|P_1[m,n]-P_2[m,n]|$ denotes the difference between peak locations at the [m,n]-th node for the PTMS be $P_1[m,n]$ and $P_2[m,n]$ respectively. In certain embodiments, if Node Aligner 1102 finds $\Theta[m,n] \leq \Theta$, then the two nodes are detected to have the same compound, and no further alignment between the nodes is needed. If Node Aligner 1102 finds $\Theta[m,n]>\Theta$, then the PTMs may need to be aligned at these nodes. Let the node with the smaller peak location be $P_1[m, n]$. Then Node Aligner 1102 extends the PTMs as follows:

(i) Keep the node at $P_1$ [m, n] at the current location.
(ii) Insert a blank node at $P_2$[m, n] and move the node originally at $P_2$[m, n] and all subsequent nodes one element down the $n^{th}$ column in the PTM matrix. The presence of a blank node indicates absence or too little presence of the compound in $P_1$ [m, n] in $P_2$.

The above procedure may be followed by Node Aligner 1102 for all nodes in ascending order down their respective columns, across all columns. Thus, the PTMs are aligned such that the respective elements in the PTM matrices typically represent one of the three possibilities:
(i) nodes containing the same compound, or
(ii) a node in one indicating a compound, and a blank node in the other indicating its absence, or
(iii) blank nodes in both indicating no further peaks occur along the particular column of the matrix.

The alignment threshold $\Theta$ described above aligns PTM nodes to represent same compounds that elute at different times in the vertical dimension of a GC×GC chromatogram due to variability. In some embodiments, it may not ensure immunity of the PTM nodes against variability in the horizontal dimension (x-axis), which may be significantly less than in the vertical dimension (y-axis), but nonetheless may need to be considered. To ensure the PTMs are synced against variability in both dimensions, Node Aligner 1102 initially vertically aligns the PTMs as discussed above. The vertical alignment threshold may be denoted as $\Theta_v$ and similarly, a horizontal alignment threshold $\Theta_h$ based on expected variability in horizontal retention times. The vertically aligned PTM nodes $P_1$ [m,n] and $P_2$ [m,n] may include corresponding peak values as p1 and p2, and corresponding GC×GC peak positions as $G_1[m_1,n_1]$ and $G_2[m_2,n_2]$. Note that due to variability, the actual GC×GC peak positions in the vertically aligned nodes $P_1$[m, n] and $P_2$[m, n] may differ to within a vertical range of $\Theta_v$ and a horizontal range of $\Theta_h$. In certain embodiments, Node Aligner 1102 ensures the vertically aligned peaks $p_1$ and $p_2$ stored in the [m,n]-th node of the PTMs are also aligned to within the horizontal spread $\Theta_h$ of the compound. In order to do so, Node Aligner 1102 horizontally aligns $p_1$ and $p_2$ based on a similarity threshold $\theta$. First, Node Aligner 1102 calculates the peak ratio p[m,n] given as:

$$\rho[m, n] = \max\left(\frac{p_1}{p_2}, \frac{p_2}{p_1}\right). \quad (1)$$

If Node Aligner 1102 finds p≤θ, the two peaks are considered similar enough for fingerprinting purposes, and no further horizontal alignment is necessary. If Node Aligner 1102 finds p>θ, Node Aligner 1102 modifies $p_1$ and $p_2$ to the aligned values $p_1$ and $p_2$ to reflect the maximum value the signal from the compound obtains within the horizontal spread to provide fair comparison between the peaks. Mathematically, this step may be expressed as:

$$\tilde{p}_i = \max_{m \in (-\Theta_v, \Theta_v), n \in (-\Theta_h, \Theta_h)} G_i(m_i + m, n_i + n), \quad (2)$$

where $i = 1, 2$.

The aligned PTM nodes now reflect peak values aligned to the maximum value attained within a vertical spread of $\Theta_v$ and a horizontal spread $\Theta_h$ respectively. In some embodiments, Node Aligner 1102 performs the vertical alignment procedure described above followed by the horizontal alignment procedure described above. In some embodiments, Node Aligner 1102 performs the horizontal alignment procedure described above followed by the vertical alignment procedure described above. In some embodiments, Node Aligner 1102 performs joint vertical and horizontal alignment, whereby the PTMs are aligned vertically and horizontally at substantially the same time. For example, Node Aligner 1102 may interleave steps from the horizontal and vertical alignment procedures for joint alignment of the PTMs.

Next, PTM Analyzer 1100 passes the aligned PTMs to PTM Comparator 1104. PTM Comparator 1104 evaluates a given comparison metric between individual peaks that appear at corresponding nodes in their respective PTMs, and computes a comprehensive measure over the comparison metric measured across hundreds of peaks within the two-dimensional GC×GC image. In other words, PTM Comparator 1104 extends comparisons based on a given metric between individual peaks to a comprehensive measure that spans across the entire spectrum of the two-dimensional GC×GC image. Assuming $p_1$ and $p_2$ are peaks at aligned non-blank nodes of two PTMs being compared, PTM Comparator 1104 may use one or more of the following three metrics denoted below:

$$\rho_1(p_1, p_2) = \max\left(\frac{p_1}{p_2}, \frac{p_2}{p_1}\right), \quad (3)$$

$$\rho_2(p_1, p_2) = \max\left|\log\left(\frac{p_1}{p_2}\right)\right|, \quad (4)$$

and $$\rho_3(p_1, p_2) = (p_1 - p_2)^2. \quad (5)$$

Assuming $P_1$(m, n) and $P_2$(m,n) denote the aligned non-blank nodes at the [m,n]-th element of two PTMs, PTM Comparator 1104 may combine any of the above metrics as a filtered sum denoted below:

$$S = \sum_{n=1}^{N} \sum_{m=1}^{M} \frac{(P_1(m, n) + P_2(m, n))}{2} (\rho(P_1(m, n), P_2(m, n)), \quad (6)$$

The filtered sum across the PTMs generates a quantitative measure for comparing two oil samples based on their PTMs. The filtered sum may account for the difference in bigger peaks to matter more in the distinction but include the hundreds of smaller peaks in the topography to contribute to the measure.

In some embodiments, PTM Comparator 1104 employs a topography map filtering (TMF) measure that is a filtered sum of comparison metrics that helps compare non-blank nodes, i.e., where the same compound has a well-formed peak (but may have varying peak values), in the PTMs under consideration. PTM Comparator 1104 trains a two-dimensional filter to weigh the peaks based on their relative dispersion around the mean value for a training set of samples which are assumed to represent the source. PTM Comparator 1104 may then form a source template PTM based on training set of samples. For example, the training set may be a collection of oil samples from a source oil well, and the source template PTM may represent the oil source. Mathematically, the comparison metric may be chosen from equations (3), (4) or (5) for any comparison between non-blank nodes. Assuming $P_s$ and $P_t$ respectively denote the PTMs of the unknown sample to be fingerprinted (to determine the source of a given sample)

and the template PTM for the source fingerprint. The filtered sum $S_{TMF}$ is computed, similar to equation (6) for a given comparison metric p(·) as follows:

$$S_{TMF}(P_s, P_t) = \sum_{n=1}^{N}\sum_{m=1}^{M} \frac{1}{\sigma(m,n)} \frac{(P_s(m,n) + P_t(m,n))}{2} (\rho(P_s(m,n), P_t(m,n)), \quad (8)$$

where σ(m, n) denotes the standard deviation of the training sample peak values around the template average for a non-blank node at the [m,n]-th element. Introduction of σ(m, n) may account for dispersion in peak values for certain PTM nodes within samples from the same source, thus making the measure relatively immune to which training set was chosen for the trial.

The TMF approach to fingerprinting (to determine the source of a given sample) may work well for separation between sources that are distinct enough around the higher peaks such that the difference in the filtered sum between sample offers a clear dynamic range for distinction between sources. In the event the sources exhibit similar topography over the higher well-investigated peaks, as is common for sources that share geographic proximity, the filtered sum in equation (7) may be modified to include a mask that considers only the peaks that are sufficiently dissimilar. The masking matrix Δ may be chosen to suppress any peaks that are similar past a pre-designed threshold τ between the sample and template to highlight the differences between the sample to be tested against the template. Mathematically, the mask matrix may be denoted as:

$$\Delta(m,n) = \begin{cases} 1 & \text{if } \rho(P_s(m,n), P_t(m,n)) < \tau \\ 0 & \text{else} \end{cases} \quad (8)$$

The masked filtered sum may now be expressed as:

$$S_{TMF}(P_s, P_t) = \sum_{n=1}^{N}\sum_{m=1}^{M} \Delta(m,n) \frac{1}{\sigma(m,n)} \frac{(P_s(m,n) + P_t(m,n))}{2} (\rho(P_s(m,n), P_t(m,n)), \quad (9)$$

The TMF approach may be particularly convenient when enough training samples are available for the comparison, e.g. to test for connectivity between sources, so that sufficient data is available to estimate a and the source PTM robustly and have a data-driven idea to set τ high or low enough to successfully separate closely related sources.

In some embodiments, PTM Comparator 1104 performs direct comparisons between aligned PTMs to facilitate measurements that quantify the similarity and differences between the GC×GC topography of two samples, or two injections from the same sample. Such collective interpretation based on direct PTM comparisons may address the question of what aspects of two oil samples are a match, and where do they differ, based on the entire biomarker topography of their GC×separations. Subsequent to node alignment between the two PTMs, PTM Comparator 1104 may evaluate a comparison metric defined between individual aligned PTM nodes and compute a comprehensive measure over this comparison metric measured across all PTM nodes. This may allow extending comparisons between individual compounds at a given PTM node to a comprehensive measure that spans across the entire topography of the samples. Assuming $p_1$ and $p_2$ are peaks at aligned non-blank nodes of the two PTMs being compared, the metric for individual peak comparisons may be based on equation (3) described above.

Assuming $P_1(m,n)$ and $P_2(m,n)$ denote the aligned non-blank nodes at the $[m,n]^{th}$ element of two PTMs, PTM Comparator 1104 may threshold the comparison metric at a pre-chosen value, τ, and classify the distribution of peaks between the aligned PTMs into two classes: (i) $C_{dissimilar}(P_1,P_2,\tau)$ including peaks $p_1 \epsilon P_1$ and $p_2 \epsilon P_2$ that measure $\rho(p_1, p_2) \geq \tau$, and (ii) $C_{similar}(P_1,P_2,\tau)$ including peaks $p_1 \epsilon P_1$ and $p_2 \epsilon P_2$ that measure $\rho(p_1, p_2) < \tau$. PTM Comparator 1104 may calculate a threshold-driven metric, S, directly compare two aligned PTMs $P_1$ and $P_2$ as follows:

$$S(\tau, P_1, P_2) = \frac{\sum_{n=1}^{N}\sum_{m=1}^{M} I_{m,n}\rho(P_1(m,n), P_2(m,n))}{\sum_{n=1}^{N}\sum_{m=1}^{M} \rho(P_1(m,n), P_2(m,n))}, \quad (10)$$

where I is an indicator function for choosing the $C_{similar}(P_1, P_2,\tau)$ class as follows:

$$I_{m,n} = \begin{cases} 1, & \text{if } \rho(P_1(m,n), P_2(m,n)) \geq \tau \\ 0 & \text{else} \end{cases}$$

The metric S may have a value between 0 and 1, the metric allowing for measuring the percentage of peaks between the PTMs that are classified as "similar" with respect to the chosen threshold τ. In some embodiments, the indicator function I may be modified to calculate the similar peaks that have high values at a higher weight than those at lower values, or as suitably desired. The modified indicator function may be using a scaled weighing function w(·) that highlights larger peaks over smaller peaks as:

$$I_{m,n} = \begin{cases} w(\text{mean}(P_1(m,n), P_2(m,n))), & \text{if } \rho(P_1(m,n), P_2(m,n)) \geq \tau \\ 0 & \text{else} \end{cases}$$

The above informational method provides direct comparison across GC×GC images based on their PTMs, while including the traditional peak comparisons in the major compounds. The weighted indicator function accounts for the difference in bigger peaks to matter more in the distinction but the overall metric S may also include the hundreds of smaller peaks in the topography to contribute to the measure.

Figure 12A:
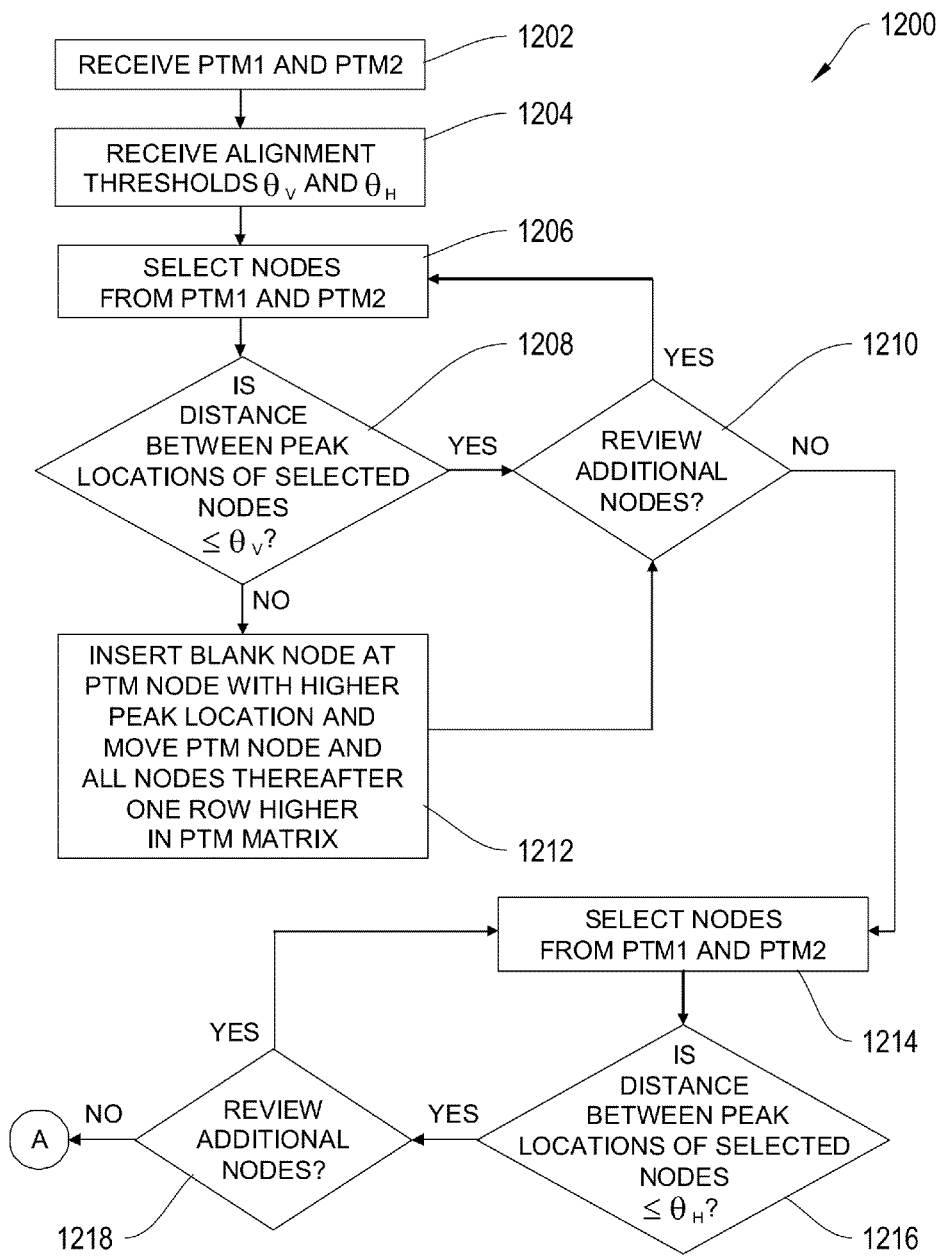
FIGS. 12A-12B depict an illustrative flow diagram for comparing two PTMs at the PTM analyzer of FIG. 11.
Figure 12B:
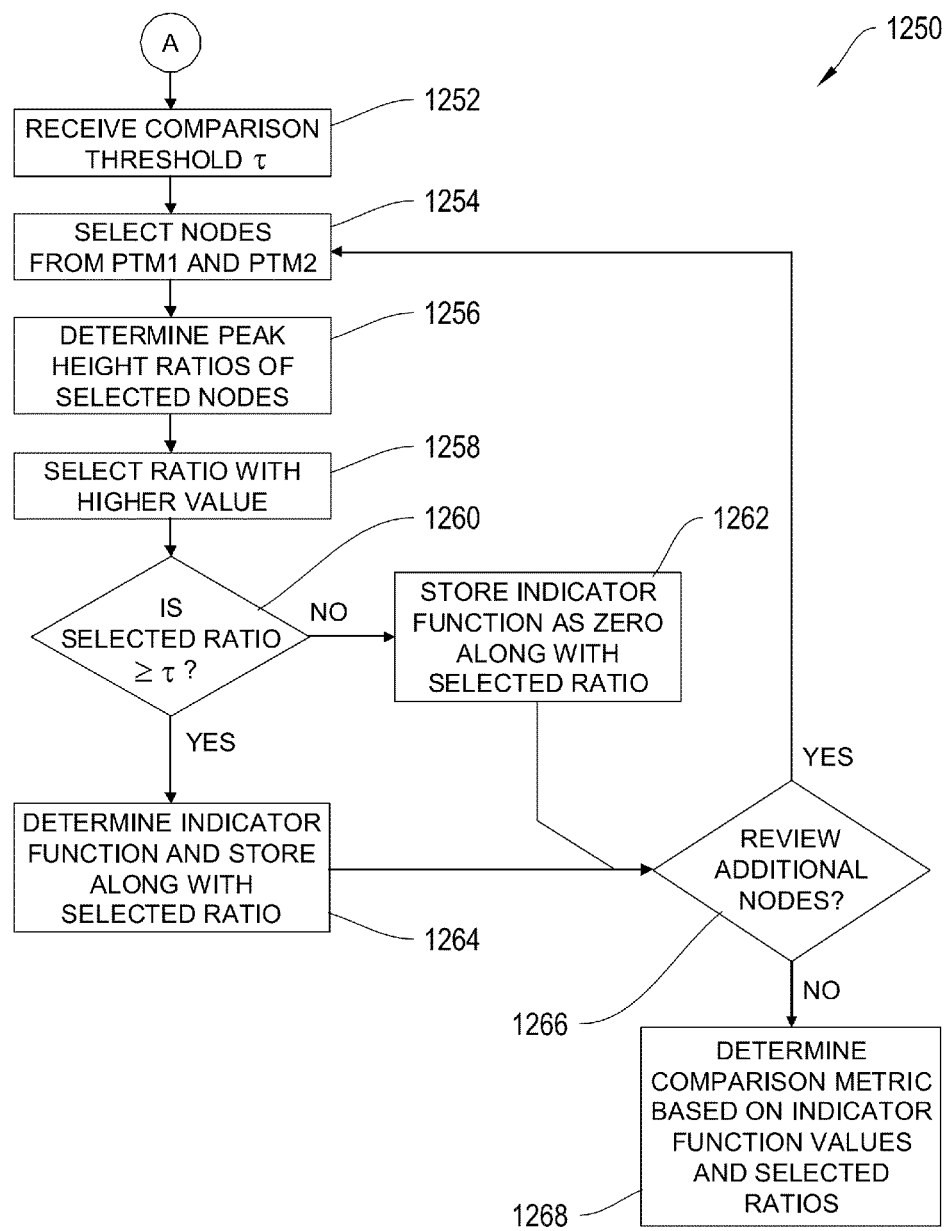

FIGS. 12A-12B depict illustrative flow diagrams 1200 and 1250 for comparing PTMs at the PTM Analyzer 1100. The PTM Analyzer 1100 and its components may be implemented on a computer system, e.g., system 200 of FIG. 2. At step 1202, PTM Analyzer 1100 receives two PTMs, PTM1 and PTM2, for comparison. In some embodiments, PTM Analyzer 1100 may receive three or more PTMs for comparison. At step 1204, PTM Analyzer 1100 receives at least one of a vertical alignment threshold $\Theta_v$ and a horizontal alignment threshold $\Theta_h$. The thresholds may be received via user input, preset function, or any other suitable input. At step 1206, PTM Analyzer 1100 passes the PTMs along with the received alignment thresholds to Node Aligner 1102. Node Aligner 1102 performs node alignment as described above with respect to FIG. 11. At step 1206, Node Aligner 1102 selects corresponding nodes from the PTMs for vertical alignment. At step 1208, Node Aligner 1102 compares the distance between peak locations of the selected nodes to vertical alignment threshold $\Theta_v$. If the distance is less than or equal to vertical alignment threshold $\Theta_v$, Node Aligner 1102 considers the nodes aligned and moves on to step 1210. If the distance is greater than vertical alignment threshold $\Theta_v$, Node Aligner 1102 performs node alignment as described above with respect to FIG. 11.

At step 1212, Node Aligner 1102 inserts a blank node at the PTM node having a higher peak location, and moves the PTM node and all nodes thereafter one row higher in the PTM. Node Aligner 1102 then proceeds to step 1210. At step 1210, Node Aligner 1102 reviews if any additional nodes remain to be considered for vertical alignment. If so, Node Aligner 1102 returns to step 1206. If no additional nodes remain to be considered for vertical alignment, Node Aligner 1102 moves to step 1214. At step 1214, Node Aligner 1102 selects corresponding nodes from the PTMs for horizontal alignment. At step 1216, Node Aligner 1102 compares the distance between peak locations of the selected nodes to horizontal alignment threshold $\Theta_h$. If the distance is less than or equal to horizontal alignment threshold $\Theta_h$, Node Aligner 1102 considers the nodes aligned and moves on to step 1218. If the distance is greater than horizontal alignment threshold $\Theta_h$, Node Aligner 1102 performs node alignment as described above with respect to FIG. 11. Node Aligner 1102 then proceeds to step 1218. At step 1218, Node Aligner 1102 reviews if any additional nodes remain to be considered for vertical alignment. If so, Node Aligner 1102 returns to step 1214. If no additional nodes remain to be considered for vertical alignment, Node Aligner 1102 moves to step 1252.

At step 1252, Node Aligner 1102 passes the aligned PTMs to PTM Comparator 1104. PTM Comparator 1104 receives a comparison threshold $\tau$. The threshold may be received via user input, preset function, or any other suitable input. The comparison threshold $\tau$ helps determine the variability in peak height that may be considered when comparing PTM nodes. At step 1254, PTM Comparator 1104 selects corresponding nodes from the PTMs for comparison. At step 1256, PTM Comparator 1104 determines a ratio of peak heights of the respective nodes, including a ratio of a first peak height to a second peak height and vice versa. At step 1258, PTM Comparator 1104 selects the ratio with higher value. At step 1260, PTM Comparator 1104 compares the selected ratio against comparison threshold $\tau$. If the selected ratio is greater than or equal to comparison threshold $\tau$ at step 1264, determines an indicator function (e.g., equation (8)) based on the ratio and stores the determined indicator along with the selected ratio for later retrieval. If the selected ratio is less than comparison threshold $\tau$, at step 1262, PTM Comparator 1104 stores the indication function as zero along with the selected ratio for later retrieval. From both steps 1262 and 1264, PTM Comparator 1104 moves to step 1266 and reviews whether any additional nodes remain in the PTMs for comparison. If so, PTM Comparator 1104 returns to step 1254. If no additional nodes remain in the PTMs for comparison, PTM Comparator 1104 retrieves the stored indication function and ratio values, and determines a comparison metric based on the retrieved values. For example, PTM Comparator 1104 may compute the filtered sum indicated in equation (9).

Figure 13:
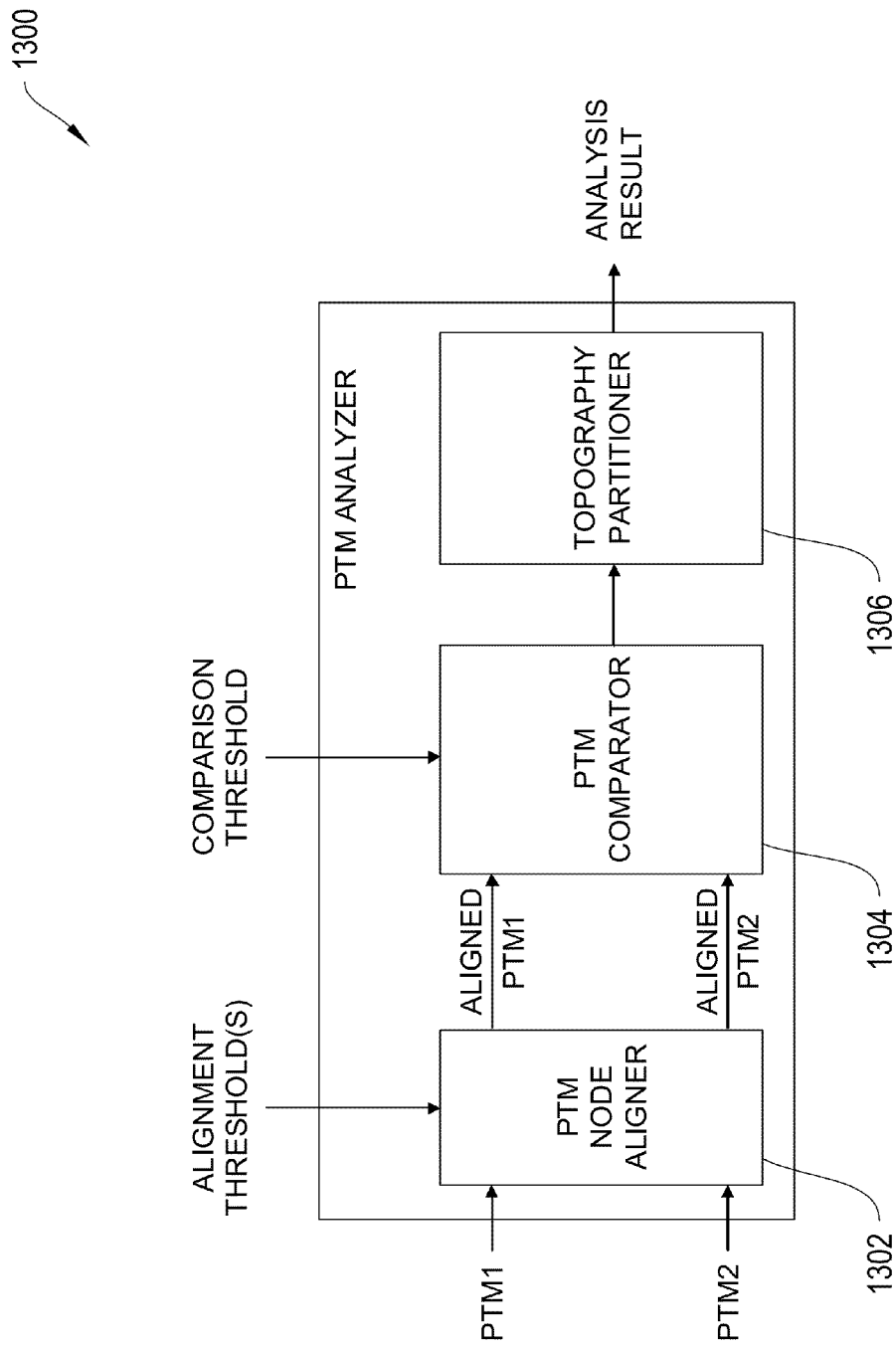
FIG. 13 depicts a block diagram for another illustrative embodiment of a PTM analyzer including a Topography Partitioner.

In some embodiments, the systems and methods described herein include topography partitioning for peak-to-peak comparisons between PTMs of different chemical mixtures, e.g., different oil samples. This is a topography-based measure that combine traditional analysis of a few well-know peaks with several less-explored peaks that are typically unused for interpretation of chromatography images. The topography partitioning measure visually represents peak-to-peak comparisons between a source PTM and a target PTM by splitting the target PTM into two graphs: a similarity partition graph that illustrates peaks similar to the source PTM, and a dissimilarity partition graph that illustrates peaks dissimilar to the source PTM. In some embodiments, any peak information including one or more of peak value, peak location, peak volume, and the peak order (described in reference FIG. 5) may be used for the peak-to-peak comparison. FIG. 13 depicts a block diagram for an illustrative PTM Analyzer 1300 including a Topography Partitioner 1306. The PTM Analyzer 1300 may be implemented on a computer system, e.g., system 200 if FIG. 2, according to illustrative flow diagrams 1400 and 1450 of FIGS. 14A-14B. Node Aligner 1302 and PTM Comparator 1304 may be similar to. Node Aligner 1102 and PTM Comparator 1104 described with respect to FIG. 11 above. However, PTM analyzer 1300 includes a Topography Partitioner 1306 that may be used for source fingerprinting and determining source connectivity by partitioning a GC×GC image into separate sections based on similarity and dissimilarity thresholds with respect to the source topography map. In some ways, the masking technique described above (for suppressing any peaks that are similar past a given threshold between the sample and template) is extended to partition the GC×GC image into "similar" and "dissimilar" classes. Topography Partitioner 1306 may classify a peak at the [k.l]-th aligned node of a PTM as "similar" or "dissimilar" to another PTM according to a chosen comparison metric $p(\cdot)$ as follows:

$$P_s(k, l) \Longrightarrow \begin{cases} \text{"dissimilar"} & \text{if } \rho(P_s(k, l), P_t(k, l)) > \tau \\ \text{"similar"} & \text{if } \rho(P_s(k, l), P_t(k, l)) \le \tau \end{cases} \quad (10)$$

The above partition rule implicitly assumes the aligned nodes are both non-blank. When both nodes are blank, this signifies neither PTM column has any peak at this node location. This generally does not lend itself to comparison between the sample and the source as neither node represents a real compound. In fact, blank nodes for a given column for both PTMs also indicate that there are no further peak in subsequent nodes, as the nodes store peak locations in ascending order, and the comparison metric should be computed for the next column. However, the scenario changes when only one of nodes is blank, denoting the absence of a peak or a peak that is not well-formed in the sample for a given compound in the source, or the presence of a compound in the sample that is not commonly found in the source. This clearly indicates a difference between the source and the sample, and Topography Partitioner 1306 may classify aligned nodes where one node is blank as "dissimilar."

In some embodiments, for each topography partition for a given similarity (or dissimilarity) threshold, Topography Partitioner 1306 may instead calculate the percentage of peak volume that falls within or outside the threshold. For example, Topography Partitioner 1306 may integrate the peak volume along the vertical dimension for a given peak, and if the peak ratio for the peak compared to the source falls outside the comparison threshold $\tau$, the peak volume may be put into the dissimilarity partition. The percentage may now be calculated as $100-P_{dissimilar}$, where $P_{dissimilar}$ is the percent of the GC×GC spread being investigated that falls outside the threshold $\tau$. In some embodiments, Topography Partitioner 1306 varies $\tau$ in (10) and establishes a threshold-dependent similarity (or dissimilarity) classification of the GC×GC spread of a given oil sample with respect to a known source.

Figure 14A:
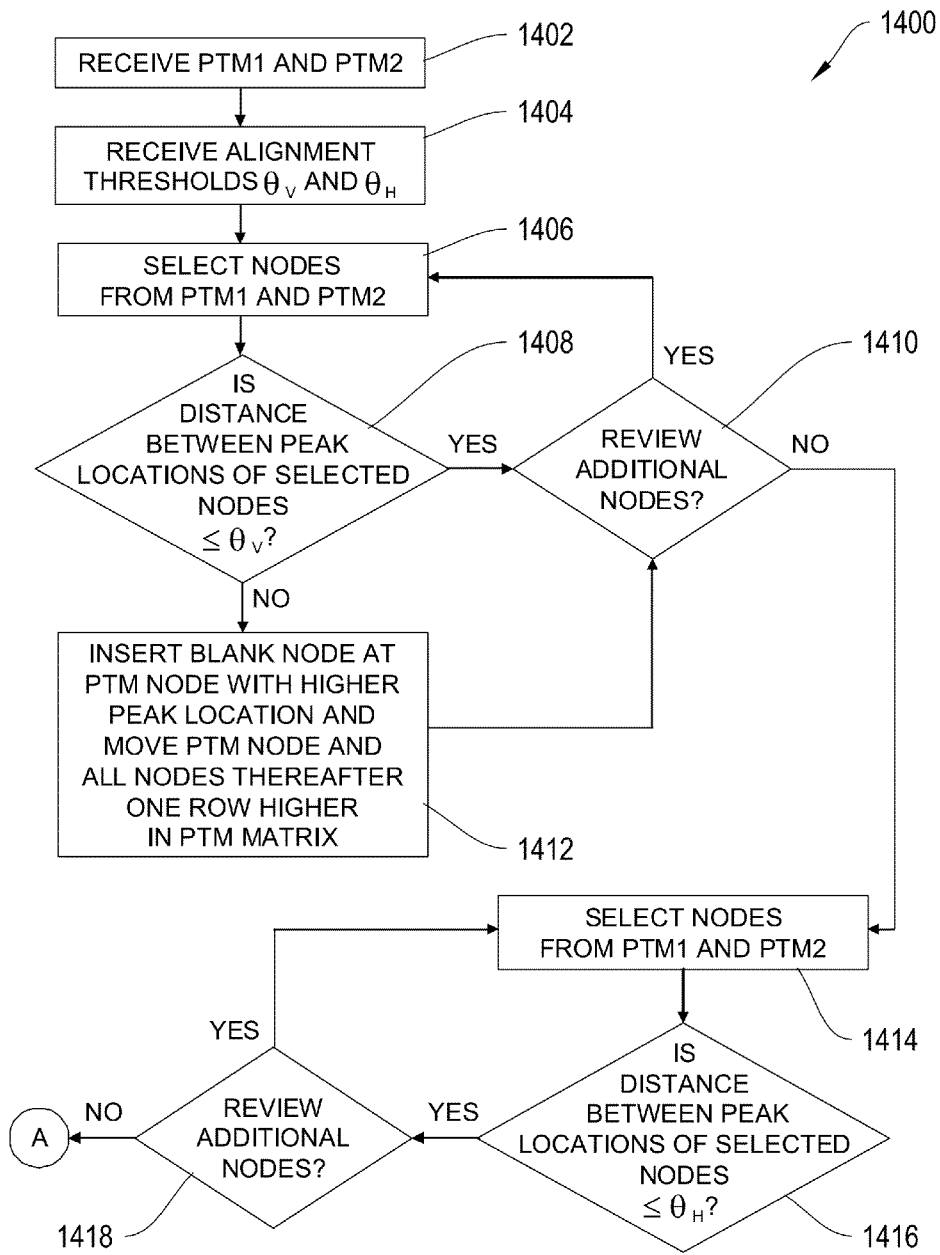
FIGS. 14A-14B depict an illustrative flow diagram for comparing two PTMs at the PTM analyzer of FIG. 13.
Figure 14B:
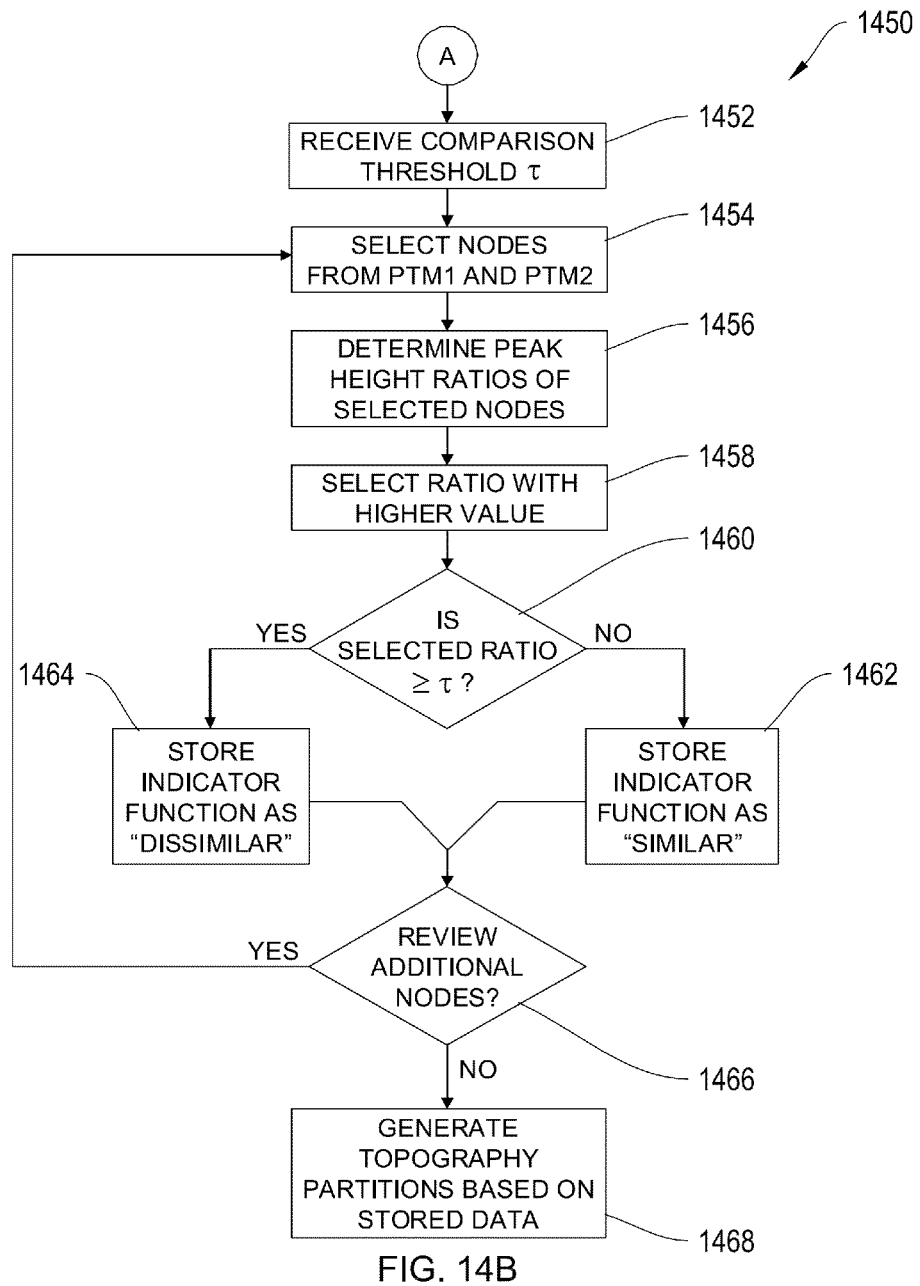

FIGS. 14A-14B depict illustrative flow diagrams 1400 and 1450 for comparing PTMs via the PTM Analyzer 1300. The PTM Analyzer 1300 and its components may be implemented on a computer system, e.g., system 200 of FIG. 2. At step 1402, PTM Analyzer 1300 receives two PTMs, PTM1 and PTM2, for comparison. In some embodiments, PTM Analyzer 1300 may receive three or more PTMs for comparison. At step 1404, PTM Analyzer 1300 receives at least one of a vertical alignment threshold $\Theta_v$ and a horizontal alignment threshold $\Theta_h$. The thresholds may be received via user input, preset function, or any other suitable input. At step 1406, PTM Analyzer 1300 passes the PTMs along with the received alignment thresholds to Node Aligner 1302. Node Aligner 1302 performs node alignment as described above with respect to FIG. 11. At step 1406, Node Aligner 1302 selects corresponding nodes from the PTMs for vertical alignment. At step 1408, Node Aligner 1302 compares the distance between peak locations of the selected nodes to vertical alignment threshold $\Theta_v$. If the distance is less than or equal to vertical alignment threshold $\Theta_v$, Node Aligner 1302 considers the nodes aligned and moves on to step 1410. If the distance is greater than vertical alignment threshold $\Theta_v$, Node Aligner 1302 performs node alignment as described above with respect to FIG. 11.

At step 1412, Node Aligner 1302 inserts a blank node at the PTM node having a higher peak location, and moves the PTM node and all nodes thereafter one row higher in the PTM. Node Aligner 1302 then proceeds to step 1410. At step 1410, Node Aligner 1302 reviews if any additional nodes remain to be considered for vertical alignment. If so, Node Aligner 1302 returns to step 1406. If no additional nodes remain to be considered for vertical alignment, Node Aligner 1302 moves to step 1414. At step 1414, Node Aligner 1302 selects corresponding nodes from the PTMs for horizontal alignment. At step 1416, Node Aligner 1302 compares the distance between peak locations of the selected nodes to horizontal alignment threshold $\Theta_h$. If the distance is less than or equal to horizontal alignment threshold $\Theta_h$, Node Aligner 1302 considers the nodes aligned and moves on to step 1418. If the distance is greater than horizontal alignment threshold $\Theta_h$, Node Aligner 1302 performs node alignment as described above with respect to FIG. 11. Node Aligner 1302 then proceeds to step 1418. At step 1418, Node Aligner 1302 reviews if any additional nodes remain to be considered for vertical alignment. If so, Node Aligner 1302 returns to step 1414. If no additional nodes remain to be considered for vertical alignment, Node Aligner 1302 moves to step 1452.

At step 1452, Node Aligner 1302 passes the aligned PTMs to PTM Comparator 1304. PTM Comparator 1304 receives a comparison threshold τ. The threshold may be received via user input, preset function, or any other suitable input. The comparison threshold τ helps determine the variability in peak height that may be considered when comparing PTM nodes. At step 1454, PTM Comparator 1304 selects corresponding nodes from the PTMs for comparison. At step 1456, PTM Comparator 1304 determines a ratio of peak heights of the respective nodes, including a ratio of a first peak height to a second peak height and vice versa. At step 1458, PTM Comparator 1304 selects the ratio with higher value. At step 1460, PTM Comparator 1304 compares the selected ratio against comparison threshold τ. If the selected ratio is greater than or equal to comparison threshold r, at step 1464, determines an indicator function (e.g., equation (10)) based on the ratio and stores the determined indicator (e.g., "dissimilar") along with the selected ratio for later retrieval. If the selected ratio is less than comparison threshold τ, at step 1462, PTM Comparator 1304 determines an indicator function (e.g., equation (10)) based on the ratio and stores the determined indicator (e.g., "similar") along with the selected ratio for later retrieval. From both steps 1462 and 1464, PTM Comparator 1304 moves to step 1466 and reviews whether any additional nodes remain in the PTMs for comparison. If so, PTM Comparator 1304 returns to step 1454. If no additional nodes remain in the PTMs for comparison, PTM Comparator 1304 retrieves the stored indication function and ratio values, and passes them to Topography Partitioner 1306.

At step 1468, Topography Partitioner 1306 generates one or more topography partitions for the dataset. For example, Topography Partitioner 1306 may generate topography partitions as described below with reference to FIGS. 15A-15C. The x-axis and y-axis of each sub-figure shows the retention times in the horizontal and vertical dimensions respectively and the z-axis shows the peak magnitude normalized to the highest peak value. In this example, a source template PTM is derived based on sixteen samples from the BP spill source: one taken from the Macondo well prior to the BP spill, and the rest taken after the spill. FIGS. 15A-15C depict illustrative topography partitions 1500-1580 for an oil sample collected from Eugene Island, a related source within the area but distinct from the BP spill source. The source template PTM is used as the basis for the partitioning, i.e., the Eugene Island sample is being compared to the source template PTM. While FIG. 15A shows the Eugene Island PTM, FIG. 15B and FIG. 15C demonstrate the similarity and dissimilarity partitions, respectively, with respect to threshold τ=1.85 against the Macondo well source (source of the BP oil spill), which serves as the source PTM for the partitioning. The topography partitioning measure visually represents peak-to-peak comparisons between the source template PTM and the Eugene Island PTM by splitting the Eugene Island PTM into two graphs: a similarity partition graph that illustrates peaks similar to the source template PTM (FIG. 15B), and a dissimilarity partition graph that illustrates peaks dissimilar to the source template PTM (FIG. 15C).

FIG. 16 depicts an illustrative two-way comparison matrix 1600 of thirty eight samples against each other. In particular, in FIG. 16, GC×GC images corresponding to thirty-eight independent injections across thirty-three oil samples collected from a variety of sources are compared against each other. The gray-scaled value in the [k,1]-th element of the cross=comparison matrix in FIG. 3 represent comparison metric, S, to measure the degree of similarity between the two PTMs representing GC×GC images #k and #1 respectively. The grey-scale image is calibrated between 0 and 100 with 100 being the lightest. As expected, the cross-comparison matrix visualized in FIG. 16, that the diagonal that represents the direct comparison of an injection to itself are all 100. Injections from samples originating from the same source score values close to 100, compared to samples that do not co-originate.

As noted above, in FIG. 16, GC×GC images corresponding to thirty-eight independent injections across thirty-three oil samples collected from a variety of sources are compared against each other. The comparisons are based on aligned PTMs corresponding to any two injections and visualized in the grey-scale two-way cross-comparison matrix. The thirty-eight injections considered span across thirty-three separate samples which originate from a variety of source reservoirs, including the Macondo well (GC×GC image indices #1, #8, #9, #11, #13, #17, #26 through #37) before and after the Gulf of Mexico oil spill. In particular, the GC×GC image indices (#8, #17, #26) and #35 correspond to independent non-consecutive injections of a sample taken directly from the broken riser pipe at the Macondo well with a special collector on Jun. 21, 2010; GC×GC image #11 corresponds to a surface sample from the Macondo well collected after the spill; GC×GC image #13 is a separate sample collected directly from the broken riser pipe; GC×GC images #1 and #9 correspond to independent injections of a pre-spill sample taken directly from the Macondo well; GC×GC images #27, #28, #29, #30, #31, #32,#33,#34,#36 and #37 correspond to ten separate oil samples from the Macondo well spill collected from grass blades along the Gulf of Mexico coast; and GC×GC images #10 and #16 correspond to samples taken from other petroleum sources within geographic proximity (within 160 km.) of the Macondo well. The remaining samples are from sources much farther from and unrelated to the Macondo well.

Comparing between the PTMs of GC×GC image indices #2, #3, and #4 (see Table 2 below), which are independent consecutive injections of the same sample (NIST 1582, a standard reference oil from the National Institute of Standards and Technology: likely from Monterey Shale), it is observer that the PTMs corresponding to the independent injections score high values when compared to each other, with a mean of 88.84 and a standard deviation of 2.27. The standard deviation being much lower than the order of the mean indicates a high level of statistical tolerance for achieving a close match between the consecutive injections. Therefore, we conclude that the direct PTM method is robust for testing closeness of match between consecutive injections from the same sample.

TABLE 2

Cross-comparison values between the PTMs of three independent and consecutive injections of the same NIST sample (listed as GC × GC images #2, #3, and #4 in FIG. 16)

| Injection ID | Injection 1 | Injection 2 | Injection 3 |
|---|---|---|---|
| Injection 1 | 100.00 | 86.26 | 90.49 |
| Injection 2 | 86.26 | 100.00 | 89.78 |
| Injection 3 | 90.49 | 89.78 | 100.00 |

Comparing between non-consecutive injections from one sample from the Macondo well (four independent non-consecutive injections of a sample taken directly from the broken riser pipe at the Macondo well with a special collector on Jun. 21, 2010), it is observed that cross-PTM comparisons score high values with a mean of 93.23 mean and a low standard deviation of 2.7, indicating a high level of statistical tolerance for obtaining a close match between non-consecutive injections for this sample. The injections were spaced several days apart and therefore indicate that the direct PTM comparison is robust against variability under different experimental conditions.

Comparing across different Macondo well samples (all injections from Macondo well samples taken pre-spill and post-spill from a variety of collection points), it is observed that cross-PTM comparisons score high values with a mean of 91.79 mean and a low standard deviation of 3.77, indicating a high level of statistical tolerance for obtaining a close match between samples that originate from the same source, in this case, the Macondo well. This indicates that the direct PTM comparison is robust against variability under different collection points and independent injections of samples that originate in the same source.

Next, a comparison between injections from different samples of closely related sources is observed, including six PTMs corresponding to injections from (i) three separate samples collected from the same source: Macondo well pre-spill sample (GC×GC image #1) and post-spill samples (GC×GC image indices #17 and #11), all of which originate from the Macondo well; (ii) two samples collected from distinct sources within the vicinity of the Macondo well: Eugene Island sample (GC×GC image #16) and Southern Louisiana crude oil (GC×GC image #10); and (iii) one sample (GC×GC image #6) from Kamchatka (Russia), which has completely different origin from sources in the Gulf of Mexico. The injections corresponding to GC×GC images #1, #11, and #17 derive from the Macondo well and score high cross-comparison values with respect to each other with low standard deviation (mean=90.39, standard deviation=0.6). They also score lower values with higher standard deviation when compared against injections #16 (mean=85.11, standard deviation=5.92) and #10 (mean=66.14, standard deviation=9.2), which derive from a distinct sources within the Gulf of Mexico locale. Though the injections #16 and #17 score closely when directly compared against each other, the significantly lower variation of sample #17 against other samples from Macondo well establishes its origin from the same source. This conclusion is further supported below by investigating the broader question of what makes these two injections similar, and where they differ based on evaluating 2 at the individual compounds.

Figure 17:
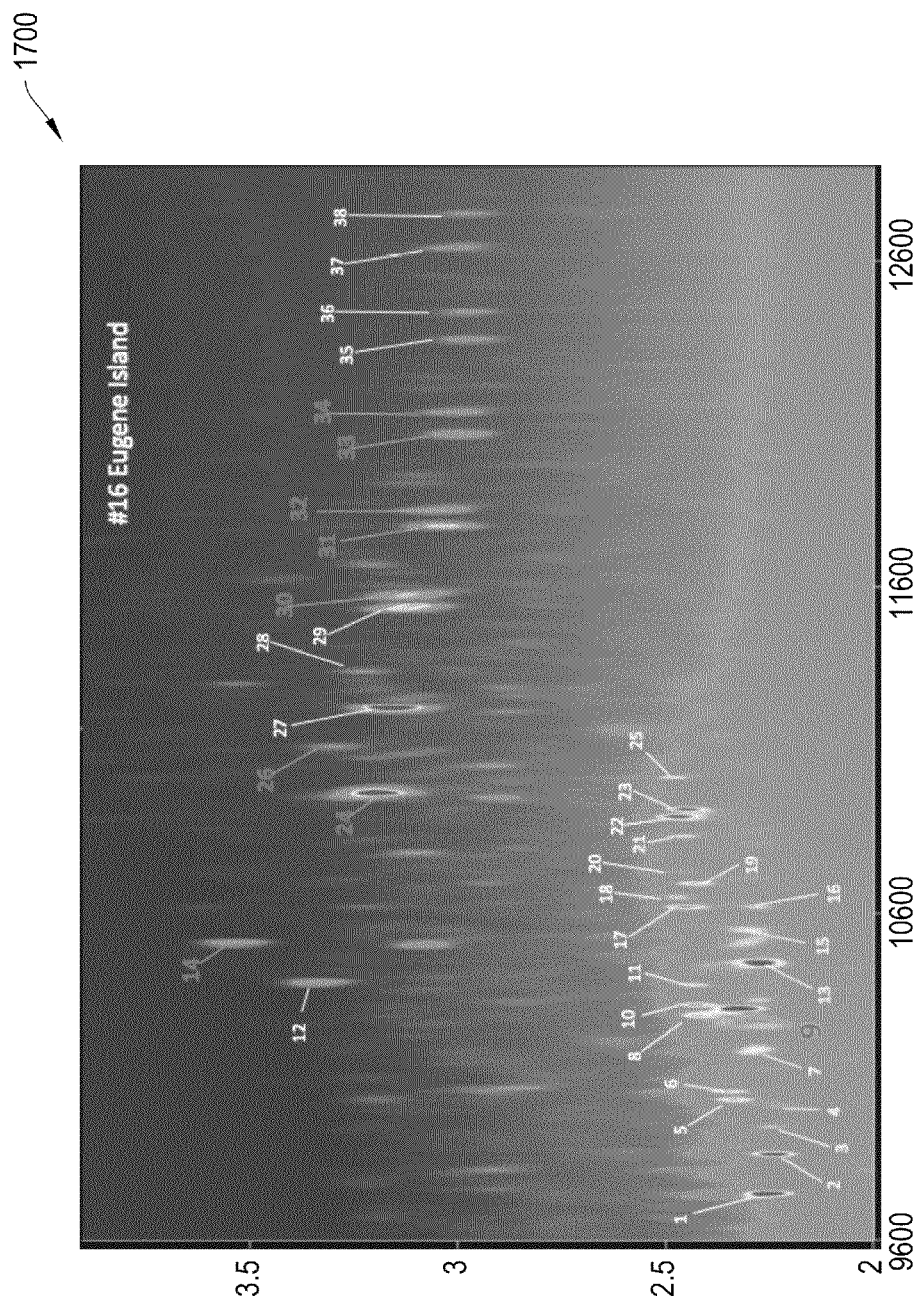
FIG. 17 depicts a GC×GC image of injection #16 in FIG. 16 labeling the major compounds.

FIG. 17 illustrates the GC×GC image 1700 of injection #16 labeling the major compounds (see Table 1 above for compound names). The compounds that occur in similar proportions between the two samples, i.e., the metric falls below the threshold τ, have smaller yellow labels, and the compounds that differ in their proportions, i.e., the metric exceeds τ, have larger pink labels. A significant number of major compounds differ in their relative proportions between these two injections, justifying a different origin for the oil samples, which conforms to traditional analysis based on only the major compounds. However, based on the collective interpretation of the topography it is observed that the two injections, despite significant differences in some major compounds, exhibits collective similarity, indicative of similar locale of origin. All samples from the Gulf of Mexico locale, i.e., samples #1, #10, #11, #16 and #17, score appropriately low values against oil from Kamchatka (Russia) in sample #6 (mean=19.22, standard deviation=1.85). Therefore, we conclude that the samples of identical origin manifest the least deviation about a high mean comparison value, thus differentiating them against samples that are from distinct sources within geographic proximity. Samples that are completely unrelated to a given locale exhibit significantly lower comparison values against samples that originate in that locale. The direct PTM comparison method offers insights into what aspects of GC×GC topography relate to a particular source, or a given locale spanning related but multiple sources, and provides a broader definition of petroleum fingerprint distinct to a given reservoir or a broader locale.

In some embodiments, the systems and methods described herein may be utilized to determine the source of a target oil sample. A database of oil source PTMs may be collected beforehand, and the PTM of the target oil sample may be compared against the source PTMs in the database to find a match. Even if an exact match is not found, the resulting analysis (e.g., topography partitions) may help determine the oil source having samples most similar to the target sample.

In some embodiments, the systems and methods described herein may be utilized to determine whether two oil samples are from the same oil source. For example, a first sample may be from a given oil well in a first location, and a second sample may be collected from a second, different location. If the two samples match, there may be high probability that sources for both samples are connected underground, and a new oil well need not be constructed in the second location. Knowing how closely related sources are may guide placement of oil wells.

In some embodiments, the systems and methods described herein may be utilized to track how far a target oil sample has moved from its source. For example, if the target oil sample found at a first location matches a reference sample from a second, different location, it may indicate that the target oil sample has traveled from the second location to the first location. Such an analysis may be relevant in the case of oil spills to help determine how far the oil has seeped into the environment.

In some embodiments, the systems and methods described herein may be utilized to determine how related to oil sources are to another. For example, given source template PTMs for two oil sources, the PTMs may be compared to determine how closely related or different the two sources are.

In some embodiments, the systems and methods described herein can advantageously be used to compare two chemical samples by comparing their PTMs. In such embodiments, the PTM comparison may not depend on where the chemical samples came from. In certain other embodiments, the systems and methods described herein can be used to compare the PTM of a chemical sample against a source template PTM. The source template PTM may be constructed from one or more PTMs obtained from samples from the same source. For example, a source template PTM may be base on a plurality of PTMs, each obtained from GC×GC measurements of different samples from the same source. Such an embodiment may provide a system that may be reliable and statistically robust. Such embodiments may be used to determine if the chemical sample originated from a given source. In other embodiments, PTMs generated from multiple sources may be compared against each other, i.e., a source template PTM may be compared against another source template PTM.

In some embodiments, the systems and methods described herein may be utilized to compare PTMs of: (i) two samples from an identical source, (ii) two samples from two genetically close but distinct sources, (iii) two samples from two clearly different sources, and (iv) two different runs (e.g., GC×GC analysis) of a given sample. As has been demonstrated above, the PTM-based approach is robust and capable of performing such analysis accurately.

The systems and methods described herein may be realized as a software component operating on a conventional data processing system such as a Unix workstation. In that embodiment, these mechanisms can be implemented as a C language computer program, or a computer program written in any high level language including Matlab, C++, Fortran, Java or BASIC. Additionally, in an embodiment where microcontrollers or DSPs are employed, the mapping mechanism 22 can be realized as a computer program written in microcode or written in a high level language and compiled down to microcode that can be executed on the platform employed. The development of such data processing systems is known to those of skill in the art, and such techniques are set forth in Digital Signal Processing Applications with the TMS320 Family, Volumes I, II, and III, Texas Instruments (1990). Additionally, general techniques for high level programming are known, and set forth in, for example, Stephen G. Kochan, *Programming in C*, Hayden Publishing (1983). It is noted that DSPs are particularly suited for implementing signal processing functions, including preprocessing functions such as image enhancement through adjustments in contrast, edge definition and brightness. Developing code for the DSP and microcontroller systems follows from principles well known in the art. The system also provides and enables as is known to those of skill in the art, object oriented frameworks are generally understood as a set of classes that embody a design for solutions to a family of related problems. See *The C++ Programming Language*, 2nd Ed., Stroustrup Addison-Wesley. Accordingly, a framework for mapping a filtering may be created that provides a prefabricated structure, or template, of a working mapping and filtering program.

Variations, modifications, and other implementations of what is described may be employed without departing from the spirit and scope of the systems and methods described herein. For example, though the systems and methods are described in the context of fingerprinting oil samples, the systems and methods may be equally applicable for analyzing other chemical mixtures, such as dissolved organic matter in pond scum or other chemical mixtures having dissolved organic matter. The analysis may be used for studying phenomena such as carbon cycling or pollution effects on such chemical mixtures. Moreover, any of the method and system features described above or incorporated by reference may be combined with any other suitable method or system feature disclosed herein or incorporated by reference, and is within the scope of the contemplated systems and methods. The systems and methods may be embodied in other specific forms without departing from the spirit or essential characteristics thereof. The foregoing embodiments are therefore to be considered in all respects illustrative, rather than limiting of the systems and methods described herein.

What is claimed is:

1. A method for comparing samples, each having a plurality of compounds, comprising:

receiving a reference dataset representing a relative separation of a plurality of compounds included in a reference sample;

receiving a target dataset representing a relative separation of a plurality of compounds included in a target sample;

creating a reference topography map based on the reference dataset, wherein the reference topography map has topographic variations and includes a plurality of peaks representing one or more compounds;

creating a target topography map based on the target dataset, wherein the target topography map has topographic variations and includes a plurality of peaks representing one or more compounds;

identifying peak information for each peak in the reference topography map and the target topography map, wherein peak information for each peak includes at least one of a peak height, a peak location, a peak volume, and a peak order;

calculating a comparison metric for each pair of corresponding peaks in the reference topography map and the target topography map based on the identified peak information;

generating a similarity partition based on the calculated comparison metrics that represents a similarity in topographic variations between the reference topography map and the target topography map; and generating a dissimilarity partition based on the calculated comparison metrics that represents a dissimilarity in topographic variations between the reference topography map and the target topography map.

2. The method of claim 1, wherein the similar partition includes one or more peaks from the target dataset that are similar to corresponding peaks in the reference data set.

3. The method of claim 1, comprising:
   receiving, at a region selector, an indication of a region of interest in the reference dataset;
   extracting, at the region selector, the region of interest for use as the reference dataset.

4. The method of claim 1, wherein the reference dataset and the target dataset include one of a comprehensive two-dimensional gas chromatogram, a one-dimensional gas chromatogram, a gas chromatogram and mass-spectrogram (GC-MS), a liquid chromatogram and gas chromatogram (LC×GC), and a two-dimensional liquid chromatogram (LC×LC).

5. The method of claim 1, wherein the reference sample and the target sample are oil samples, and each sample includes a plurality of biomarker compounds.

6. The method of claim 5, wherein the plurality of biomarker compounds includes hopanes and steranes.

7. The method of claim 1, comprising receiving a comparison threshold at the PTM analyzer, and determining the similarity index based on the comparison threshold.

8. The method of claim 1, further comprising calculating a similarity index using more than one of the comparison metrics.

9. The method of claim 1, wherein the reference dataset and the target dataset include substantially all peaks representing their respective plurality of compounds.

10. A system for comparing samples, each having a plurality of compounds, comprising:
   a peak topography map (PTM) generator configured to:
      receive a reference dataset representing a relative separation of a plurality of compounds included in a reference sample;
      receive a target dataset representing a relative separation of a plurality of compounds included in a target sample;
      create a reference topography map based on the reference dataset, wherein the reference topography map has topographic variations and includes a plurality of peaks representing one or more compounds;
      create a target topography map based on the target dataset, wherein the target topography map has topographic variations and includes a plurality of peaks representing one or more compounds;
   a peak analyzer configured to:
      identify peak information for each peak in the reference topography map and the target topography map, wherein peak information for each peak includes at least one of a peak height, a peak location, a peak volume, and a peak order;
   a PTM analyzer configured to:
      calculate a comparison metric for each pair of corresponding peaks in the reference topography map and the target topography map based on the identified peak information; and
   a topography partitioner configured to:
      generate a similarity partition based on the calculated comparison metrics that represents a similarity in topographic variations between the reference topography map and the target topography map;
      generate a dissimilarity partition based on the calculated comparison metrics that represents a dissimilarity in topographic variations between the reference topography map and the target topography map.

11. The system of claim 10, wherein the similar partition includes one or more peaks from the target dataset that are similar to corresponding peaks in the reference data set.

12. The system of claim 10, further comprising:
   a region selector configured to:
      receive an indication of a region of interest in the reference dataset;
      extract the region of interest for use as the reference dataset.

13. The system of claim 10, wherein the reference dataset and the target dataset include one of a comprehensive two-dimensional gas chromatogram, a one-dimensional gas chromatogram, a gas chromatogram and mass-spectrogram (GC-MS), a liquid chromatogram and gas chromatogram (LC×GC), and a two-dimensional liquid chromatogram (LC×LC).

14. The system of claim 10, wherein the reference sample and the target sample are oil samples, and each sample includes a plurality of biomarker compounds.

15. The system of claim 14, wherein the plurality of biomarker compounds includes hopanes and steranes.

16. The system of claim 10, wherein the PTM analyzer is further configured to receive a comparison threshold, and determine the similarity index based on the comparison threshold.

17. The system of claim 10, wherein the reference dataset and the target dataset include substantially all peaks representing their respective plurality of compounds.

18. The system of claim 10, wherein the PTM analyzer is further configured to calculate a similarity index using more than one of the comparison metrics.

19. A method for comparing samples, each having a plurality of compounds, comprising:
   receiving a reference dataset representing a relative separation of a plurality of compounds included in a reference sample wherein the reference dataset has topographic variations includes a plurality of peaks representing one or more compounds;
   receiving a target dataset representing a relative separation of a plurality of compounds included in a target sample, wherein the target dataset has topographic variations includes a plurality of peaks representing one or more compounds;
   identifying peak information for each peak in the reference dataset and the target dataset, wherein peak information for each peak includes at least one of a peak height, a peak location, a peak volume, and a peak order;
   generating a reference peak topography map (PTM) based on the identified reference peak information, the reference PTM having one or more nodes storing reference peak information;
   generating a target PTM based on the identified target peak information, the target PTM having one or more nodes storing target peak information; and
   calculating a comparison metric for each pair of corresponding peaks in the reference PTM and the target PTM based on peak information stored in the reference PTM and the target PTM.

20. The method of claim 19, comprising aligning, at a node aligner, the reference PTM and the target PTM based on comparison metrics of selected corresponding nodes from each PTM.

21. The method of claim 20, wherein aligning the reference PTM and the target PTM comprises inserting one or more nodes in proximity of the selected nodes in one of the reference PTM and the target PTM based on the comparison metrics of the selected nodes.

22. The method of claim 19, comprising:
   selecting a subsection of one of the reference PTM and target PTM;
   analyzing peak information of a plurality of nodes in the subsection;

in response to determining one or more nodes having lower peaks in proximity to at least one node having a higher peak, generating a clustered node combining the nodes having the lower peaks and the at least one node having the higher peak.

23. The method of claim 19, comprising:
generating, at a topography partitioner, a similarity partition based on the similarity index that represents a similarity in topographic variations between the reference dataset and the target dataset;
generating, at the topography partitioner, a dissimilarity partition based on the similarity index that represents a dissimilarity in topographic variations between the reference dataset and the target dataset.

24. The method of claim 19, further comprising calculating a similarity index using more than one of the comparison metrics.

25. A system for comparing samples, each having a plurality of compounds, comprising:
a peak topography map (PTM) generator configured to:
  receive a reference dataset representing a relative separation of a plurality of compounds included in a reference sample, wherein the reference dataset has topographic variations and includes a plurality of peaks representing one or more compounds;
  receive a target dataset representing a relative separation of a plurality of compounds included in a target sample, wherein the target dataset has topographic variations and includes a plurality of peaks representing one or more compounds;
a peak analyzer configured to:
  identify peak information for each peak in the reference dataset and the target dataset, wherein peak information for each peak includes at least one of a peak height, a peak location, a peak volume, and a peak order;
a matrix generator configured to:
  generate a reference peak topography map (PTM) based on the identified reference peak information, the reference PTM having one or more nodes storing reference peak information;
  generate a target PTM based on the identified target peak information, the target PTM having one or more nodes storing target peak information; and
a PTM analyzer configured to:
  calculate a comparison metric for each pair of corresponding peaks in the reference PTM and the target PTM based on peak information stored in the reference PTM and the target PTM.

26. The system of claim 25, further comprising a node aligner configured to align the reference PTM and the target PTM based on comparison metrics of selected corresponding nodes from each PTM.

27. The system of claim 26, wherein aligning the reference PTM and the target PTM comprises inserting one or more nodes in proximity of the selected nodes in one of the reference PTM and the target PTM based on the comparison metrics of the selected nodes.

28. The system of claim 25, further comprising a cluster analyzer configured to:
select a subsection of one of the reference PTM and target PTM;
analyze peak information of a plurality of nodes in the subsection;
in response to determining one or more nodes having lower peaks in proximity to at least one node having a higher peak, generate a clustered node combining the nodes having the lower peaks and the at least one node having the higher peak.

29. The system of claim 25, further comprising a topography partitioner configured to:
generate a similarity partition based on the similarity index that represents a similarity in topographic variations between the reference dataset and the target dataset;
generate a dissimilarity partition based on the similarity index that represents a dissimilarity in topographic variations between the reference dataset and the target dataset.

30. The system of claim 25, wherein the PTM analyzer is further configured to calculate a similarity index using more than one of the comparison metrics.

\* \* \* \* \*

UNITED STATES PATENT AND TRADEMARK OFFICE
CERTIFICATE OF CORRECTION

| | | |
|---|---|---|
| PATENT NO. | : 8,838,393 B2 | Page 1 of 1 |
| APPLICATION NO. | : 13/437759 | |
| DATED | : September 16, 2014 | |
| INVENTOR(S) | : Ananta Sen Gupta, Christopher M. Reddy and Robert Nelson | |

It is certified that error appears in the above-identified patent and that said Letters Patent is hereby corrected as shown below:

In the specification

In Column 1, line 14 before "Background" the following should be inserted:

--STATEMENT OF RIGHTS TO INVENTIONS MADE UNDER FEDERALLY SPONSORED RESEARCH
This invention was made with Government support under Grant No. 0950670 awarded by the National Science Foundation. The Government has certain rights in this invention.--

Signed and Sealed this
Thirty-first Day of May, 2016

Michelle K. Lee
*Director of the United States Patent and Trademark Office*